United States Patent
Becker

(10) Patent No.: US 9,849,241 B2
(45) Date of Patent: Dec. 26, 2017

(54) METHOD OF OPERATING A CONTROL DEVICE FOR CONTROLLING AN INFUSION DEVICE

(71) Applicant: Fresenius Kabi Deutschland GmbH, Bad Homburg (DE)

(72) Inventor: Michael Becker, Knittlingen (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 126 days.

(21) Appl. No.: 14/786,118

(22) PCT Filed: Feb. 24, 2014

(86) PCT No.: PCT/EP2014/053548
§ 371 (c)(1),
(2) Date: Oct. 21, 2015

(87) PCT Pub. No.: WO2014/173558
PCT Pub. Date: Oct. 30, 2014

(65) Prior Publication Data
US 2016/0074582 A1    Mar. 17, 2016

(30) Foreign Application Priority Data
Apr. 24, 2013   (EP) .................................... 13165045

(51) Int. Cl.
*A61M 5/172* (2006.01)
*G06F 19/00* (2011.01)

(52) U.S. Cl.
CPC .......... *A61M 5/1723* (2013.01); *A61M 5/172* (2013.01); *G06F 19/3468* (2013.01);
(Continued)

(58) Field of Classification Search
CPC ................ A61M 5/1723; A61M 5/172; A61M 2230/43; A61M 2205/50; A61M 2230/10; A61M 2205/35; G06F 19/3468
(Continued)

(56) References Cited

U.S. PATENT DOCUMENTS

| 41,291 A | 1/1864 | Garrelson ...................... 417/512 |
| 4,280,494 A | 7/1981 | Cosgrove, Jr. et al. ...... 128/213 |

(Continued)

FOREIGN PATENT DOCUMENTS

| CN | 2620531 U | 6/2004 | ............... A61B 5/00 |
| CN | 201049111 | 4/2008 | ............... A61M 5/00 |

(Continued)

OTHER PUBLICATIONS

Schwilden, et al., Closed-loop feedback control of propofol anaesthesia by quantative EEG analysis in humans, date of publication: 1989.*

(Continued)

*Primary Examiner* — Manuel Mendez
(74) *Attorney, Agent, or Firm* — Cook Alex Ltd.

(57) ABSTRACT

Method of operating a control device for controlling an infusion device A method of operating a control device (2) for controlling an infusion device (33) for administering a drug to a patient (P) comprises the steps of: providing a model (p) to predict a time-dependent drug concentration (Cplasma, Clung, Cbrain) in multiple compartments (A1-A5) of a patient (P); setting a target concentration value (CTbrain) to be achieved in at least one of the compartments (A1-A5) of the patient (P); determining a drug dosage (D1) to be administered to a first compartment (A1) of the multiple compartments (A1-A5) of the patient (P) using the model (p) such that the difference between the target con- (Continued)

centration value (CTbrain) and a predicted steady-state drug concentration (Cplasma, Clung, Cbrain) in the at least one of the compartments (A1-A5) is smaller than a pre-defined threshold value (Ub-rain); providing a control signal (S1) indicative of the drug dosage (D1) to an infusion device (33) for administering the drug dosage (D1) to the patient (P); obtaining a measurement value (M1, M2) indicating a measured drug concentration in a second compartment (A2, A3) of the multiple compartments (A1-A5) at a measurement time (t1, t2); adjusting the model (p) such that the model (p) predicts a drug concentration (Clung, Cbrain) in the second compartment (A2, A3) at the measurement time (t1, t2) which at least approximately matches the measured drug concentration in the second compartment (A2, A3); and determining a new drug dosage (D2, D3) to be administered into the first compartment (A1) of the patient (P) using the model (p) such that the difference between the target concentration value (CT-brain) and a predicted steady-state drug concentration (Cplasma, Clung, Cbrain) in the at least one of the compartments (A1, A2, A3) is smaller than the pre-defined threshold value (Ubrain). In this way a method is provided which allows for an improved (personalized and predictive) control of a drug administration procedure, in particular when administering an anaesthetic drug such as Propofol and/or an analgesic drug such as Remifentanil within a procedure.

16 Claims, 12 Drawing Sheets

(52) U.S. Cl.
CPC ..... *A61M 2205/35* (2013.01); *A61M 2205/50* (2013.01); *A61M 2230/10* (2013.01); *A61M 2230/43* (2013.01)

(58) Field of Classification Search
USPC .............. 604/65–67, 151, 131; 128/DIG. 12, 128/DIG. 13
See application file for complete search history.

(56) References Cited

U.S. PATENT DOCUMENTS

| | | | |
|---|---|---|---|
| 4,533,346 A | 8/1985 | Cosgrove, Jr. et al. | 604/66 |
| 4,590,065 A | 5/1986 | Piechota, Jr. et al. | 424/49 |
| 5,458,117 A | 10/1995 | Chamoun et al. | 128/734 |
| 5,775,330 A | 7/1998 | Kangas et al. | 128/731 |
| 5,807,316 A | 9/1998 | Teeple, Jr. | 604/51 |
| 5,846,208 A | 12/1998 | Pichlmayr et al. | 600/544 |
| 6,016,444 A | 1/2000 | John | 600/544 |
| 6,032,072 A | 2/2000 | Greenwald et al. | 600/544 |
| 6,067,467 A | 5/2000 | John | 600/544 |
| 6,117,075 A | 9/2000 | Barnea | 600/300 |
| 6,128,521 A | 10/2000 | Marro et al. | 600/383 |
| 6,157,857 A | 12/2000 | Dimpfel | 600/544 |
| 6,178,522 B1 | 1/2001 | Zhou et al. | 714/12 |
| 6,301,493 B1 | 10/2001 | Marro et al. | 600/383 |
| 6,315,736 B1 | 11/2001 | Tsutsumi et al. | 600/500 |
| 6,317,627 B1 | 11/2001 | Ennen et al. | 600/544 |
| 6,338,713 B1 | 1/2002 | Chamoun et al. | 600/300 |
| 6,394,953 B1 | 5/2002 | Devlin et al. | 600/383 |
| 6,430,437 B1 | 8/2002 | Marro | 600/544 |
| 6,526,297 B1 | 2/2003 | Merilainen | 600/310 |
| 6,599,281 B1 | 7/2003 | Struys et al. | 604/503 |
| 6,605,072 B2 | 8/2003 | Struys et al. | 604/503 |
| 6,631,291 B2 | 10/2003 | Viertio-Oja et al. | |
| 6,654,626 B2 | 11/2003 | Devlin et al. | 600/383 |
| 6,685,649 B2 | 2/2004 | Korhonen | 600/485 |
| 6,731,975 B1 | 5/2004 | Viertio-Oja et al. | 600/544 |
| 6,745,764 B2 | 6/2004 | Hickle | 128/203.12 |
| 6,801,803 B2 | 10/2004 | Viertio-Oja | 600/544 |
| 6,807,965 B1 | 10/2004 | Hickle | 128/204.23 |
| 6,868,345 B1 | 3/2005 | Jensen | 702/32 |
| 6,882,166 B2 | 4/2005 | Shambroom et al. | 324/692 |
| 6,894,359 B2 | 5/2005 | Bradley et al. | 257/414 |
| 6,934,579 B2 | 8/2005 | Mantzaridis et al. | 600/544 |
| 6,939,307 B1 | 9/2005 | Dunlop | 600/504 |
| 6,953,435 B2 | 10/2005 | Kondo et al. | 600/485 |
| 6,961,603 B2 | 11/2005 | Merilainen | 600/383 |
| 6,975,901 B2 | 12/2005 | Philip | 600/544 |
| 6,981,947 B2 | 1/2006 | Melker | 600/532 |
| 6,985,833 B2 | 1/2006 | Shambroom et al. | 702/191 |
| 6,986,347 B2 | 1/2006 | Hickle | 128/200.24 |
| 7,069,062 B2 | 6/2006 | Minotani et al. | 455/575.6 |
| 7,089,927 B2 | 8/2006 | John et al. | 128/200.24 |
| 7,104,963 B2 | 9/2006 | Melker et al. | 600/532 |
| 7,130,673 B2 | 10/2006 | Tolvanen-Laakso et al. | 600/383 |
| 7,161,362 B2 | 1/2007 | Shambroom et al. | 324/692 |
| 7,195,780 B2 | 3/2007 | Dennis et al. | 424/502 |
| 7,201,734 B2 | 4/2007 | Hickle | 604/67 |
| 7,215,994 B2 | 5/2007 | Huiku | 600/544 |
| 7,220,240 B2 | 5/2007 | Struys et al. | 604/65 |
| 7,228,169 B2 | 6/2007 | Viertio-Oja | 600/544 |
| 7,229,430 B2 | 6/2007 | Hickle et al. | 604/57 |
| 7,231,245 B2 | 6/2007 | Greenwald et al. | 600/544 |
| 7,247,154 B2 | 7/2007 | Hickle | 604/500 |
| 7,308,894 B2 | 12/2007 | Hickle | 128/204.23 |
| 7,316,231 B2 | 1/2008 | Hickle | 128/203.13 |
| 7,364,552 B2 | 4/2008 | Kiesele | 600/532 |
| 7,367,949 B2 | 5/2008 | Korhonen et al. | 600/483 |
| 7,373,198 B2 | 5/2008 | Bibian et al. | 600/544 |
| 7,407,486 B2 | 8/2008 | Huiku et al. | 600/500 |
| 7,445,609 B2 | 11/2008 | Bunke et al. | 604/65 |
| 7,447,541 B2 | 11/2008 | Huiku | 600/544 |
| 7,449,757 B2 | 11/2008 | Bradley et al. | 257/414 |
| 7,496,400 B2 | 2/2009 | Hoskonen et al. | 600/544 |
| 7,509,161 B2 | 3/2009 | Viertio-Oja | 600/544 |
| 7,522,040 B2 | 4/2009 | Passmore et al. | 340/540 |
| 7,547,931 B2 | 6/2009 | Star et al. | 257/253 |
| 7,549,959 B2 | 6/2009 | Takala et al. | 600/300 |
| 7,556,036 B2 | 7/2009 | Bouillon et al. | 128/203.15 |
| 7,565,905 B2 | 7/2009 | Hickle | 128/203.14 |
| 7,603,168 B2 | 10/2009 | Bibian et al. | 600/509 |
| 7,625,340 B2 | 12/2009 | Sarkela | 600/300 |
| RE41,291 E | 4/2010 | Viertio-Oja et al. | 600/544 |
| 7,693,697 B2 | 4/2010 | Westenskow et al. | 703/11 |
| 7,711,417 B2 | 5/2010 | John et al. | 600/544 |
| 7,714,398 B2 | 5/2010 | Ben-Barack et al. | 257/414 |
| 7,725,173 B2 | 5/2010 | Viertio-Oja et al. | 600/544 |
| 7,725,174 B2 | 5/2010 | Kern et al. | 600/544 |
| 7,774,052 B2 | 8/2010 | Burton et al. | 600/544 |
| 7,783,343 B2 | 8/2010 | Sarkela et al. | 600/545 |
| 7,805,187 B2 | 9/2010 | Sarkela et al. | 600/544 |
| 7,811,247 B2 | 10/2010 | Hengstenberg et al. | 604/66 |
| 7,820,108 B2 | 10/2010 | Lampotang et al. | 422/84 |
| 7,844,324 B2 | 11/2010 | Sarkela et al. | 600/544 |
| 7,860,561 B1 | 12/2010 | Modarres | 600/544 |
| 7,860,583 B2 | 12/2010 | Condurso et al. | 700/2 |
| 7,878,982 B2 | 2/2011 | Frank et al. | 600/557 |
| 7,899,525 B2 | 3/2011 | John et al. | 600/544 |
| 7,920,914 B2 | 4/2011 | Shieh et al. | 600/544 |
| 7,925,338 B2 | 4/2011 | Huiku | 600/544 |
| 7,937,138 B2 | 5/2011 | Liley | 600/544 |
| 7,948,041 B2 | 5/2011 | Bryant et al. | 257/414 |
| 7,955,559 B2 | 6/2011 | Joshi et al. | 422/68.1 |
| 7,956,525 B2 | 6/2011 | Armitage et al. | 313/309 |
| 7,985,181 B2 | 7/2011 | Haar et al. | 600/301 |
| 7,986,996 B2 | 7/2011 | Bell | 607/45 |
| 7,992,556 B2 | 8/2011 | Hickle | 128/204.23 |
| 8,019,400 B2 | 9/2011 | Diab et al. | 600/323 |
| 8,028,694 B2 | 10/2011 | Hickle | 128/203.14 |
| 8,038,642 B2 | 10/2011 | Tolvanen-Laakso et al. | 604/19 |
| 8,038,645 B2 | 10/2011 | Edginton et al. | 604/66 |
| 8,064,993 B2 | 11/2011 | Viertio-Oja et al. | 600/544 |
| 8,108,039 B2 | 1/2012 | Saliga et al. | 600/544 |
| 8,126,528 B2 | 2/2012 | Diab et al. | 600/336 |
| 8,145,297 B2 | 3/2012 | Viertio-Oja et al. | 600/544 |
| 8,152,991 B2 | 4/2012 | Briman et al. | 205/775 |

(56) References Cited

U.S. PATENT DOCUMENTS

| | | | |
|---|---|---|---|
| 8,154,093 B2 | 4/2012 | Bradley et al. | 257/414 |
| 8,206,341 B2 | 6/2012 | Schmidt | 604/67 |
| 8,211,035 B2 | 7/2012 | Melker et al. | 600/532 |
| 8,221,330 B2 | 7/2012 | Sarkela et al. | 600/554 |
| 8,229,872 B2 | 7/2012 | Gilluly | |
| 8,340,792 B2 | 12/2012 | Condurso et al. | 700/79 |
| 8,352,023 B2 | 1/2013 | John et al. | 600/544 |
| 8,359,080 B2 | 1/2013 | Diab et al. | 600/336 |
| 8,412,295 B2 | 4/2013 | Sethi et al. | 600/322 |
| 8,417,308 B2 | 4/2013 | Sethi et al. | 600/324 |
| 8,425,745 B2 | 4/2013 | Briman et al. | 204/409 |
| 8,456,074 B2 | 6/2013 | Armitage et al. | 313/309 |
| 8,457,731 B2 | 6/2013 | Tonini | 600/544 |
| 8,463,349 B2 | 6/2013 | Diab et al. | 600/324 |
| 8,463,370 B2 | 6/2013 | Korhonen et al. | 600/544 |
| 8,512,273 B2 | 8/2013 | Rantala et al. | 604/23 |
| 8,528,546 B2 | 9/2013 | Heesch et al. | 128/200.24 |
| 8,538,705 B2 | 9/2013 | Greenwald | 702/19 |
| 8,568,327 B2 | 10/2013 | O'Brien | 600/483 |
| 8,574,156 B2 | 11/2013 | Uutela et al. | 600/301 |
| 8,608,656 B2 | 12/2013 | Greenwald et al. | 600/301 |
| 8,622,989 B2 | 1/2014 | Martin | 604/503 |
| 8,630,722 B2 | 1/2014 | Condurso et al. | 700/9 |
| 8,641,632 B2 | 2/2014 | Quintin et al. | 600/483 |
| 8,642,966 B2 | 2/2014 | Weckstrom et al. | 250/343 |
| 8,662,077 B2 | 3/2014 | Bouillon et al. | 128/203.12 |
| 8,708,905 B2 | 4/2014 | Sarkela | 600/301 |
| 8,715,193 B2 | 5/2014 | Takala et al. | 600/481 |
| 8,728,059 B2 | 5/2014 | Karst et al. | 604/890.1 |
| 8,744,779 B2 | 6/2014 | Syroid et al. | 702/19 |
| 8,754,454 B2 | 6/2014 | Bryant et al. | 257/253 |
| 8,755,856 B2 | 6/2014 | Diab et al. | 600/322 |
| 8,761,906 B2 | 6/2014 | Condurso et al. | 700/9 |
| 8,768,447 B2 | 7/2014 | Ermes et al. | 600/544 |
| 8,778,269 B2 | 7/2014 | Joshi et al. | 422/68.1 |
| 8,783,248 B2 | 7/2014 | Heinonen et al. | 128/203.14 |
| 8,798,701 B2 | 8/2014 | Izzetoglu et al. | 600/323 |
| 8,798,735 B1 | 8/2014 | Bibian et al. | 600/544 |
| 8,814,791 B2 | 8/2014 | Sethi et al. | 600/300 |
| 8,821,397 B2 | 9/2014 | Al-Ali et al. | 600/301 |
| 8,838,226 B2 | 9/2014 | Bibian et al. | 600/544 |
| 8,858,433 B2 | 10/2014 | Sethi et al. | 600/300 |
| 8,864,702 B2 | 10/2014 | Chazot et al. | 604/66 |
| 8,882,703 B2 | 11/2014 | Hickle | 604/66 |
| 8,914,102 B1 | 12/2014 | Rey et al. | 600/547 |
| 8,977,504 B2 | 3/2015 | Hovorka | 702/19 |
| 9,037,225 B1 | 5/2015 | Saliga et al. | 600/509 |
| 9,068,996 B2 | 6/2015 | Pettigrew et al. | G01N 33/948 |
| 9,069,887 B2 | 6/2015 | Gupta et al. | 604/31 |
| 9,095,653 B2 | 8/2015 | Willmann et al. | A61M 5/1723 |
| 9,108,013 B2 | 8/2015 | Puri | A61M 16/01 |
| 9,138,183 B2 | 9/2015 | McKenna et al. | A61B 5/14552 |
| 9,234,867 B2 | 1/2016 | Briman et al. | 205/777.5 |
| 2002/0082513 A1 | 6/2002 | Ennen et al. | 600/544 |
| 2003/0055355 A1 | 3/2003 | Viertio-Oja | 600/544 |
| 2004/0015091 A1 | 1/2004 | Greenwald et al. | 600/513 |
| 2004/0084047 A1 | 5/2004 | Hickle | 128/203.13 |
| 2004/0193068 A1 | 9/2004 | Burton et al. | 600/544 |
| 2004/0243017 A1 | 12/2004 | Causevic | 600/544 |
| 2005/0169798 A1 | 8/2005 | Bradley et al. | 422/57 |
| 2006/0004296 A1 | 1/2006 | Huiku et al. | 600/513 |
| 2006/0009729 A1 | 1/2006 | Bunke et al. | 604/19 |
| 2006/0009734 A1 | 1/2006 | Martin | 604/66 |
| 2006/0058700 A1 | 3/2006 | Marro et al. | 600/554 |
| 2006/0167722 A1 | 7/2006 | MRF Struys et al. | 705/3 |
| 2007/0010756 A1 | 1/2007 | Viertio-Oja | 600/544 |
| 2007/0015985 A1 | 1/2007 | Tolvanen-Laakso et al. | 600/393 |
| 2007/0118075 A1 | 5/2007 | Uutela et al. | 604/65 |
| 2007/0132043 A1 | 6/2007 | Bradley et al. | 257/414 |
| 2007/0149953 A1 | 6/2007 | Tolvanen-Laakso et al. | 604/890.1 |
| 2007/0167694 A1 | 7/2007 | Causevic et al. | 600/301 |
| 2007/0191817 A1 | 8/2007 | Martin | 604/890.1 |
| 2007/0203448 A1 | 8/2007 | Melker et al. | 604/24 |
| 2007/0208322 A1 | 9/2007 | Rantala et al. | 604/503 |
| 2007/0276281 A1 | 11/2007 | Sarkela | 600/546 |
| 2007/0282251 A1 | 12/2007 | Barvais et al. | 604/67 |
| 2008/0021345 A1 | 1/2008 | Kern et al. | 600/554 |
| 2008/0167571 A1 | 7/2008 | Gevins | 600/544 |
| 2008/0242955 A1 | 10/2008 | Uutela et al. | 600/301 |
| 2008/0317672 A1 | 12/2008 | Viertio-Oja | 424/9.2 |
| 2009/0005270 A1 | 1/2009 | Melker et al. | 506/39 |
| 2009/0101996 A1 | 4/2009 | Bradley et al. | 257/414 |
| 2009/0118697 A1 | 5/2009 | Martin | 604/503 |
| 2009/0124867 A1 | 5/2009 | Hirsh et al. | 600/301 |
| 2009/0177108 A1 | 7/2009 | Shieh et al. | 600/544 |
| 2009/0306944 A1 | 12/2009 | Willmann et al. | 703/2 |
| 2009/0326419 A1 | 12/2009 | Gonzalez Rojas et al. | 600/587 |
| 2010/0076333 A9 | 3/2010 | Burton et al. | 600/544 |
| 2010/0130834 A1 | 5/2010 | Viertio-Oja et al. | 600/301 |
| 2010/0137731 A1 | 6/2010 | Star et al. | 600/532 |
| 2010/0137789 A1 | 6/2010 | Heinonen et al. | 604/66 |
| 2010/0212666 A1 | 8/2010 | Bouillon et al. | 128/203.14 |
| 2010/0262377 A1 | 10/2010 | Jensen | 702/19 |
| 2010/0317931 A1 | 12/2010 | Sarkela | 600/301 |
| 2011/0040197 A1 | 2/2011 | Welch et al. | 600/509 |
| 2011/0066386 A1 | 3/2011 | Hong et al. | 702/23 |
| 2011/0094509 A1 | 4/2011 | Heinonen et al. | 128/203.14 |
| 2011/0105914 A1 | 5/2011 | Frank et al. | 600/483 |
| 2011/0118619 A1 | 5/2011 | Burton et al. | 600/544 |
| 2011/0125046 A1 | 5/2011 | Burton et al. | 600/544 |
| 2011/0137134 A1 | 6/2011 | Hemmerling et al. | 600/301 |
| 2011/0137297 A1 | 6/2011 | Kiani et al. | 604/890.1 |
| 2011/0152828 A1 | 6/2011 | Martin | 604/500 |
| 2011/0168177 A1 | 7/2011 | Connor | 128/203.14 |
| 2011/0208015 A1 | 8/2011 | Welch et al. | 600/301 |
| 2011/0295096 A1 | 12/2011 | Bibian et al. | 600/372 |
| 2011/0313789 A1 | 12/2011 | Kamen et al. | 705/3 |
| 2012/0010591 A1 | 1/2012 | Chazot et al. | 604/503 |
| 2012/0016252 A1 | 1/2012 | Melker et al. | 600/532 |
| 2012/0041279 A1 | 2/2012 | Freeman et al. | 600/301 |
| 2012/0053433 A1 | 3/2012 | Chamoun et al. | 600/324 |
| 2012/0088984 A1 | 4/2012 | Al-Ali et al. | 600/301 |
| 2012/0095437 A1 | 4/2012 | Hemmerling | 604/503 |
| 2012/0116195 A1 | 5/2012 | Chaum et al. | 600/345 |
| 2012/0185267 A1 | 7/2012 | Kamen et al. | 705/2 |
| 2012/0190057 A1 | 7/2012 | Gvichiya et al. | 435/29 |
| 2012/0197188 A1 | 8/2012 | Syroid et al. | 604/93.01 |
| 2012/0203087 A1 | 8/2012 | McKenna et al. | 600/322 |
| 2012/0203126 A1 | 8/2012 | Kahlman et al. | 600/532 |
| 2012/0277548 A1 | 11/2012 | Burton | 600/301 |
| 2012/0277612 A1 | 11/2012 | Li | 600/532 |
| 2012/0277613 A1 | 11/2012 | Li et al. | 600/532 |
| 2012/0296191 A1 | 11/2012 | McGrath et al. | 600/383 |
| 2013/0030267 A1 | 1/2013 | Lisogurski et al. | 600/324 |
| 2013/0144183 A1 | 6/2013 | John et al. | 600/544 |
| 2013/0150748 A1 | 6/2013 | Jensen | 600/544 |
| 2013/0177455 A1 | 7/2013 | Kamen et al. | 417/313 |
| 2013/0184676 A1 | 7/2013 | Kamen et al. | 604/506 |
| 2013/0197339 A1 | 8/2013 | Bardakjian et al. | 600/383 |
| 2013/0197693 A1 | 8/2013 | Kamen et al. | 700/244 |
| 2013/0211207 A1 | 8/2013 | Joseph et al. | 600/301 |
| 2013/0225904 A1 | 8/2013 | Gillies et al. | 600/12 |
| 2013/0237797 A1 | 9/2013 | Muller et al. | 600/407 |
| 2013/0245568 A1 | 9/2013 | Kerr | 604/264 |
| 2013/0253362 A1 | 9/2013 | Scheib | 600/544 |
| 2013/0276785 A1 | 10/2013 | Melker et al. | 128/204.23 |
| 2013/0296823 A1 | 11/2013 | Melker et al. | 604/503 |
| 2013/0306063 A1 | 11/2013 | Manigel et al. | 128/202.16 |
| 2013/0331660 A1 | 12/2013 | Al-Ali et al. | 600/301 |
| 2013/0339049 A1 | 12/2013 | Blumberg, Jr. et al. | 705/2 |
| 2014/0012153 A1 | 1/2014 | Greenwald | 600/544 |
| 2014/0032241 A1 | 1/2014 | Coffeng | 705/3 |
| 2014/0051051 A1 | 2/2014 | O'Brien | 434/268 |
| 2014/0073860 A1 | 3/2014 | Urtti | 600/300 |
| 2014/0081094 A1 | 3/2014 | Jordan et al. | 600/301 |
| 2014/0139656 A1 | 5/2014 | Jeanne et al. | 348/77 |
| 2014/0155706 A1 | 6/2014 | Kochs et al. | 600/301 |
| 2014/0180160 A1 | 6/2014 | Brown et al. | 600/504 |
| 2014/0187973 A1 | 7/2014 | Brown et al. | 600/483 |
| 2014/0228651 A1 | 8/2014 | Causevic et al. | 600/301 |
| 2014/0288454 A1 | 9/2014 | Paz et al. | 600/532 |
| 2014/0303464 A1 | 10/2014 | Izzetoglu et al. | 600/328 |

(56) References Cited

U.S. PATENT DOCUMENTS

| | | | |
|---|---|---|---|
| 2014/0316217 A1 | 10/2014 | Purdon et al. | 600/301 |
| 2014/0316218 A1 | 10/2014 | Purdon et al. | 600/301 |
| 2014/0323898 A1 | 10/2014 | Purdon et al. | 600/544 |
| 2014/0323900 A1 | 10/2014 | Bibian et al. | 600/544 |
| 2014/0364758 A1 | 12/2014 | Schindhelm et al. | 600/531 |
| 2014/0371548 A1 | 12/2014 | Al-Ali et al. | 600/301 |
| 2014/0378784 A1 | 12/2014 | Kiani et al. | 600/301 |
| 2015/0005594 A1 | 1/2015 | Chamoun et al. | 600/301 |
| 2015/0008486 A1 | 1/2015 | Bryant et al. | 257/253 |
| 2015/0038940 A1 | 2/2015 | Kreuer et al. | 604/503 |
| 2015/0080754 A1 | 3/2015 | Purdon et al. | 600/544 |
| 2015/0119848 A1 | 4/2015 | Chaum et al. | G01N 27/3275 |
| 2015/0154364 A1 | 6/2015 | Biasi et al. | G06F 19/327 |
| 2015/0164412 A1 | 6/2015 | Kokko | A61B 5/4821 |
| 2015/0164413 A1 | 6/2015 | Wu et al. | A61B 5/4821 |
| 2015/0208926 A1 | 7/2015 | Hseu | A61B 5/0205 |
| 2015/0220702 A1 | 8/2015 | Hovorka | G06F 19/3468 |
| 2015/0374285 A1 | 12/2015 | Chang et al. | A61B 5/4821 |
| 2016/0015281 A1 | 1/2016 | McKenna et al. | A61B 5/02055 |
| 2016/0045128 A1 | 2/2016 | Sitt et al. | A61B 5/04 |

FOREIGN PATENT DOCUMENTS

| | | | |
|---|---|---|---|
| CN | 101259015 B | 9/2008 | A61B 5/0476 |
| CN | 101301196 | 11/2008 | A61B 5/0476 |
| CN | 100453041 C | 1/2009 | A61B 5/12 |
| CN | 101449974 | 6/2009 | A61B 5/048 |
| CN | 102772205 | 11/2012 | A61B 5/0476 |
| CN | 103637798 | 3/2014 | A61B 5/0476 |
| CN | 203749411 U | 8/2014 | A61B 5/04 |
| CN | 204033933 | 12/2014 | A61M 5/172 |
| CN | 103432651 | 1/2016 | A61M 5/172 |
| EP | 926984 | 7/1999 | A61B 5/11 |
| EP | 1227753 | 8/2002 | A61B 5/00 |
| EP | 1250886 | 10/2002 | A61B 5/0476 |
| EP | 1383428 | 1/2004 | A61B 5/083 |
| EP | 1610681 | 1/2006 | A61B 5/11 |
| EP | 2055233 | 5/2009 | A61B 5/11 |
| EP | 2065697 | 6/2009 | G01N 21/35 |
| EP | 2535000 | 12/2012 | A61B 5/021 |
| EP | 2563213 | 1/2016 | A61B 5/0476 |
| ES | 2483596 | 8/2014 | A61B 5/00 |
| GB | 2480996 | 2/2015 | A61B 5/0205 |
| JP | 5-108870 | 4/1993 | G06K 9/03 |
| JP | 5-288802 | 5/1993 | G01R 31/26 |
| JP | 05-296892 | 11/1993 | G01N 1/04 |
| JP | 03185202 | 7/2001 | A61B 1/00 |
| JP | 2004-309136 | 9/2004 | A61M 21/02 |
| KR | 101079785 | 10/2011 | A61B 5/0476 |
| KR | 2012/0000370 | 1/2012 | B65D 85/100 |
| KR | 101111498 | 1/2012 | A61B 5/02 |
| KR | 20130093414 | 8/2013 | A61B 5/0476 |
| WO | WO 98/31322 | 7/1998 | A61J 3/00 |
| WO | WO 03075760 | 9/2003 | A61B 5/12 |
| WO | WO 2004054441 | 7/2004 | A61B 5/04 |
| WO | WO 2005/072792 | 8/2005 | A61M 5/00 |
| WO | WO 2006045302 | 5/2006 | A61B 5/0484 |
| WO | WO 2006122349 | 11/2006 | A61B 5/0476 |
| WO | WO 2007/114931 | 10/2007 | A61K 31/395 |
| WO | WO 2008043365 | 4/2008 | A61B 5/0484 |
| WO | WO2012/024401 A2 | 2/2012 | |
| WO | WO 2012069887 | 5/2012 | A61B 5/0476 |
| WO | WO 2013060322 | 5/2013 | A61B 5/042 |
| WO | WO 2013/160780 | 10/2013 | G01N 21/00 |
| WO | WO 2014/059418 | 4/2014 | A61B 5/04 |
| WO | WO 2014208343 | 12/2014 | A61B 5/0476 |
| WO | WO 2015069778 | 5/2015 | A61B 5/04 |
| WO | WO 2015/086020 | 6/2015 | A61B 5/05 |
| WO | WO 2015/108908 | 7/2015 | A61B 5/0476 |

OTHER PUBLICATIONS

J.M. Bailey, et al.; Adaptive and Neural Network Adaptive Control of Depth of Anesthesia During Surgery, Proceedings of the 2006 American Control Conference Minneapolis, Minnesota, USA, Jun. 14-16, 2006; pp. 3409-3414.

EH Zentrum; Multitasked Closed-loop Control in Anesthesia, IEEE Engineering in Medicine and Biology; Jan./Feb. 2001; pp. 39-53.

Mathieu Jospin, et al.; Detrended Fluctuation Analysis of EEG as a Measure of Depth of Anesthesia, IEEE Transactions on Biomedical Engineering, vol. 54, No. 5. May 2007, pp. 840-846.

Yoshihito Sawaguchi, et al.; A Model-Predictive Hypnosis Control System Under Total Intravenous Anesthesia, IEEE Transactions on Biomedical Engineering, vol. 55, No. 3, Mar. 2008, pp. 874-887.

Jin-Oh Hahn, et al.; Closed-Loop Anesthetic Drug Concentration Estimation Using Clinical-Effect Feedback, IEEE Transactions on Biomedical Engineering, vol. 58, No. 1, Jan. 2011, pp. 3-6.

Clara M. Ionescu, et al.; Variable Time-Delay Estimation for Anesthesia Control During Intensive Care, IEEE Transactions on Biomedical Engineering, vol. 58, No. 2, Feb. 2011, pp. 363-369.

Jin-Oh Hahn, et al.; A Direct Dynamic Dose-Response Model of Propofol for Individualized Anesthesia Care, IEEE Transactions on Biomedical Engineering, vol. 59, No. 2, Feb. 2012, pp. 571-578.

Alexandra Krieger, et al.; Modeling and Analysis of Individualized Pharmacokinetics and Pharmacodynamics for Volatile Anesthesia, IEEE Transactions on Biomedical Engineering, vol. 61, No. 1, Jan. 2014, pp. 25-34.

Ulrich Grouven, PhD, et al.; Correlation of Narcotrend Index, Entropy Measures, and Spectral Parameters With Calculated Propofol Effect-Site Concentrations During Induction of Propofol-Remifentanil Anaesthesia, Journal of Clinical Monitoring and Computing ,vol. 18, No. 4, 2004, pp. 231-240.

Thomas Rose; European Society for Computing and Technology in Anaesthesia and Intensive Care (Esctaic), Journal of Clinical Monitoring and Computing, vol. 20, No. 2, 2006, pp. 117-144.

Leslie C. Jameson, MD, et al.; Using EEG to Monitor Anesthesia Drug Effects During Surgery, Journal of Clinical Monitoring and Computing, 2006, pp. 445-472.

Michael R. Isley, PhD, et al.; Guidelines for Intraoperative Neuromonitoring Using Raw (Analog or Digital Waveforms) and Quantitative Electroencephalography: A Position Statement by The American Society of Neurophysiological Monitoring, Journal of Clinical Monitoring and Computing, 2009, pp. 369-390.

Pinky Dua, et al.; Modelling and multi-parametric control for delivery of anaesthetic agents, Med Bioi Eng Comput, 2010, pp. 543-553.

David G Levitt, et al.; Human physiologically based pharmacokinetic model for propofol, BMC Anesthesiology, Apr. 22, 2005, pp. 1-29.

David G Levitt; Heterogeneity of human adipose blood flow, BMC Clinical Pharmacology, Jan. 20, 2007, pp. 1-21.

Wassim M. Haddad, PhD, et al.; Closed-loop control for intensive care unit sedation, Best Practice & Research Clinical Anaesthesiology 23, 2009, pp. 95-114.

William J. Loskota, PhD; MD, Intraoperative EEG monitoring, Seminars in Anesthesia, Perioperative Medicine and Pain, 2005, pp. 176-185.

Saba Rezvaniana, et al.; Increasing Robustness of the Anesthesia Process from Difference Patient's Delay Using a State-Space Model Predictive Controller, Procedia Engineering, 2011, pp. 928-932.

Mohammad El-Bardini, et al.; Direct adaptive interval type-2 fuzzy logic controller for the multivariable anaesthesia system, Ain Shams Engineering Journal, 201 1, pp. 149-160.

A.U. Schubert, et al.; Monitoring the stress response during general anaesthesia, 2007 Mediterranean Conference on Control and Automation, Jul. 27-29, 2007, Athens—Greece, pp. T21-024.

Atieh Bamdadian, et al.; Generalized Predictive Control of depth of anesthesia by using a pharmocokinetic-pharmacodynamic model of the patient, 2008, pp. 1276-1279.

Ana Castro, et al.; Modeling State Entropy of the EEG and Auditory Evoked Potentials—Hypnotic and Analgesic Interactions, Proceedings of the 29th Annual International Conference of the IEEE EMBS Cite Internationale, Lyon, France, Aug. 23-26], 2007, pp. 1949-1952.

(56) References Cited

OTHER PUBLICATIONS

Catarina S. Nunes, et al.; Modeling Anesthetic Drugs' Pharnlacodynamic Interaction on the Bispectral Index of the EEG: the Influence of Heart Rate, Proceedings of the 29th Annual International Conference of the IEEE EMBS Cite Internationale, Lyon, France, Aug. 23-26, 2007, pp. 6479-6482.

A. Bamdadian, et al.; Controlling the Depth of Anesthesia by Using Extended DMC, Proceedings of the 2008 IEEE, CIBEC 2008, pp. 1-4.

J Albino Mendez, et al.; Model-based controller for anesthesia automation, 5th Annual IEEE Conference on Automation Science and Engineering Bangalore, India, Aug. 22-25, 2009, pp. 379-384.

Faiber Robayo, et al.; Estimating the time-delay for predictive control in general anesthesia, Chinese Control and Decision Conference, 2010, pp. 3719-3724.

Margarida Martins da Silva, et al.; Online Nonlinear Identification of the Effect of Drugs in Anaesthesia Using a Minimal Parameterization and BIS Measurements, 2010 American Control Conference Marriott Waterfront, Baltimore, MD, USA, Jun. 30-Jul. 2, 2010, pp. 4379-4384.

Nadja Bressan, et al.; Target Controlled Infusion Algorithms for Anesthesia: Theory vs Practical Implementation, 31st Annual International Conference of the IEEE EMBS Minneapolis, Minnesota, USA, Sep. 2-6, 2009, pp. 6234-6237.

Behnood Gholami; Optimal Drug Dosing Control for Intensive Care Unit Sedation Using a Hybrid Deterministic-Stochastic Pharmacokinetic and Pharmacodynamic Model, 49th IEEE Conference on Decision and Control, Hilton Atlanta Hotel, Atlanta, GA, USA, Dec. 15-17, 2010, pp. 3754-3759.

Saba Rezvanian, et al.; Controlling the Depth of Anesthesia Using Model Predictive Controller and Extended Kalman Filter, 2011, pp. 213-216.

Shahab Abdulla, et al.; Depth of Anaesthesia Patient Models and Control, Proceedings of the 2011 IEEE/ICME International Conference on Complex Medical Engineering, May 22-25, Harbin, China, 2011, pp. 37-41.

Barbara Julitta, et al.; Auto-Mutual Information Function of the EEG as a Measure of Depth of Anesthesia, 33rd Annual International Conference of the IEEE EMBS Boston, Massachusetts USA, Aug. 30-Sep. 3, 2011, pp. 2574-2577.

Clara M. Ionescu, et al.; Evaluation of a Propofol and Remifentanil Interaction Model for Predictive Control of Anesthesia Induction, 2011 50th IEEE Conference on Decision and Control and European Control Conference (CDC-ECC), Orlando, FL, USA, Dec. 12-15, 2011, pp. 7374-7379.

Ioana Nascu, et al.; Adaptive EPSAC Predictive Control of the Hypnotic Component in Anesthesia, pp. 1-6.

Shahab A. Abdulla, et al.; The Effects of Time-Delay on Feedback Control of Depth of Anesthesia, Proceedings of the IEEE-EMBS International Conference on Biomedical and Health Informatics (BHI 2012), Hong Kong and Shenzhen, China, Jan. 2-7, 2012, pp. 956-959.

Catarina S. Nunes, et al.; ARX modeling of drug effects on brain signals during general anesthesia, 2013 21st Mediterranean Conference on Control & Automation (MED) Platanias-Chania, Crete, Greece, Jun. 25-28, 2013, pp. 202-205.

Cristobal Lowery, et al.; Towards Efficient, Personalized Anesthesia using Continuous Reinforcement Learning for Propofol Infusion Control, 6th Annual International IEEE EMBS Conference on Neural Engineering, San Diego, California, Nov. 6-8, 2013, pp. 1414-1417.

Filipa N. Nogueira, et al.; A simple PK/PD model identification procedure for controller design in anesthesia, 52nd IEEE Conference on Decision and Control., Florence, Italy, Dec. 10-13, 2013, pp. 109-114.

Lorella Fanti, MD, et al.; Target-controlled propofol infusion during monitored anesthesia in patients undergoing ERCP, Gastrointestinal Endoscopy, Milan, Italy, 2004, pp. 361-366.

L. Fantia, et al.; Target-controlled infusion during monitored anesthesia care in patients undergoing EUS: Propofol alone versus midazolam plus propofol a prospective double-blind randomised controlled trial, Digestive and Liver Disease 39, 2007, pp. 81-86.

M.F.Abbod, et al.; Anaesthesia Simulator: Intelligent Monitoring and Control of Depth of Anaesthesia, The Institution of Electrical Engineers, 1998, pp. 4/1-4/5.

Jitendran Muthuswamy, M.S., et al.; Predicting Depth of Anesthesia using Bispectral Parameters in Neural Networks, 1994, pp. 1087-1088.

D. A. Linkens, et al.; Non-Linear Control for Anaesthetic Depth Using Neural Networks and Resression, pp. 410-415.

J.E. Mandel, et al.; An Adaptive Controller of Narcotic Infusion Utilizing Anesthetist Input to Close the Loop, Annual International Conference of the IEEE Engineering in Medicine and Biology Society. vol. 13, No. 5, 1991, pp. 2152-2153

Jitendran Muthuswamyk, et al.; Bispectrum Analysis of EEG of a Dog to Determine the Depth Under Halothane Anesthesia, 1999, pp. 5-6.

Richard C. Watt, et al.; Human EEG Dimensionality and Depth of Anesthesia, 1994, pp. 223-224.

N.A.M. de Beer, et al.; Multivariate Analysis of the EEG and Auditory Evoked Potentials for Monitoring Depth of Anesthesia, 1994, pp. 229-230.

Taikang Nina, et al.; Bispectral Analysis of the Rat EEG During Various Vigilance States, IEEE Transactions on Biomedical Engineering, vol. 36., No. 4., Apr. 1989, pp. 497-499.

Ashutosh Sharma, M.S., et al.; EEG Classification for Estimating Anesthetic Depth During Halothane Anesthesia, pp. 2409-2410.

Stuart R. Hameroff, et al.; EEG Monitoring for Anesthetic Depth Assessment, Physiological Measurements, 1852 IEEE Engineering in Medicine & Biology Society 10th Annual International Conference, 1998, pp. 1-2.

Nick A. Pace, MB, ChB, et al.; Anesthetic Infusion Techniques—How to Do It, I, Clin. Anesth., vol. (Suppl 1.) Sep./Oct. 1992, pp. 458-528.

H.U. Rehmana, et al.; Neural networks and nonlinear regression modelling and control of depth of anaesthesia for spontaneously breathing and ventilated patients, Computer Methods and Programs in Biomedicine 40, 1993, pp. 227-247.

C.E. Thomsen, et al.; Assessment of Anaesthetic Depth by Clustering Analysis and Autoregressive Modelling of Electroencephalograms, Computer Methods and Programs in Biomedicine, 1991, pp. 125-138.

Andrew C.N. Chen; Human Brain Measures of Clinical Pain: A Review I. Topographic Mappings, Pain, Elsevier Science Publishers B.V. 1993, pp. 115-132.

Dr. Erich Scherzer; Society Proceedings Osterreichische Gesellschaft for Electroencephalographie, Electroencephalography and Clinical Neurophysiology Elsevier Publishing Company, Amsterdam, 1969, pp. 211-214.

J Jessop, et al.; Evaluation of the Actions of General Anaesthetics in the Human Brain, Gen Pharmac vol. 23, No. 6, 1992, pp. 927-935.

T. H. Cluiton-Brock, et al.; Future developments in anaesthetic safety quo vadis?, Bailliere's Clinical Anaesthesiology—vol. 2, No. 2, Jun. 1988, pp. 419-434.

Phyllis K. Brundidge, MD, et al.; EEG-Controlled "Overdosage" of Anesthetics in a Patient with a History of Intra-anesthetic Awareness, J. Clin. Anesth., vol. 6, Nov./Dec. 1994, pp. 496-499.

Milton H. Adelman. M.D., et al.; Electroencephalography in Cardiac Surgery, From the Department of Anesthesiology, The Mount Sinai Hospital, New York, New York, Oct. 1960, pp. 763-772.

Avner Sidi. MD, et al.; Estimating Anesthetic Depth by Electroencephalography during Anesthetic Induction and Intubation in Patients Undergoing Cardiac Surgery, J. Clio. Anesth., vol. 2, Mar./Apr. 1990, pp. 101-107.

S.G. Greenhaw, et al.; Development of an expert system advisor for anaesthetic control, Computer Methods and Programs in Biomedicine, 1992, pp. 215-229.

Sanford L. Klein, DDS, MD, et al.; Electroencephalographic Monitoring During General Anesthesia, J Oral Max11lofac Surg, 1984, pp. 376-381.

D.W. Clarke, et al., Generalized Predictive Control—Part I. The Basic Algorithm, Automatica, vol. 23, No. 2, pp. 137-148, 1987.

(56) References Cited

OTHER PUBLICATIONS

Michel M.R.F. Struys, et al., Closed Loops in Anaesthesia, Best Practice & Research Clinical Anesthesiology, vol. 20, No. 1, pp. 211-220, 206.

Ngai Liu, et al, Closed-Loop Coadministration of Propofol and Remifentanil Guided by Bispectral Index: A Randomized Multicenter Study, Anesthetic Pharmacology and Preclinical Pharmacology, Mar. 2011, vol. 112, No. 3, pp. 546-557.

Valentina Sartori, et al., On-line Estimation of Propofol Pharmacodynamic Parameters, Engineering in Medicine and Biology 27th Annual Conference, Sep. 1-4, 2005., pp. 74-77.

M. Mahfouf, et al., Unconstrained and Constrained Generalised Predictive Control of Depth of Anaesthesia During Surgery, Control Engineering Practice 11 (2003), pp. 1501-1515.

Sreenivas Yelneedi, et al., A Comparative Study of Three Advanced Controllers for the Regulation of Hypnosis, Journal of Process Control 19, (2009) pp. 1458-1469.

M. Mahfouf, et al., A New Generic Approach to Model Reduction for Complex Physiologically Based Drug Models, Control Engineering Practice 10 (2002) pp. 67-81.

E. Furutani, et al, A Hypnosis and Analgesia Control System Using a Model Predictive Controller in Total Intravenous Anesthesia During Day-case Surgery, SICE Annual Conference 2010, Aug. 18-21, 2010, The Grand Hotel, Taipei, Taiwan, pp. 223-226.

European Search Report for EP application No. 13165045 dated Oct. 14, 2013.

International Search Report and Written Opinion for International Application No. PCT/EP2014/053548 dated Aug. 8, 2014.

International Preliminary Report on Patentability and Written Opinion for International Application No. PCT/EP2014/053548, dated Oct. 27, 2015.

\* cited by examiner

METHOD OF OPERATING A CONTROL DEVICE FOR CONTROLLING AN INFUSION DEVICE

CROSS-REFERENCE TO RELATED APPLICATIONS

This is a U.S. national stage application of International Patent Application No. PCT/EP2014/053548, filed Feb. 24, 2014, which claims priority to European Patent Application No. EP 13165045.9, filed Apr. 24, 2013, all of which are hereby incorporated herein by reference.

The invention relates to a method of operating a control device for controlling one or multiple infusion devices for administering one or multiple drugs to a patient and a control device for controlling one or more infusion devices for administering one or multiple drugs to a patient.

Within conventional anaesthesia, anaesthetic drugs having different effects on the brain, the spinal cord and the nervous system are administered to a patient. For example, within an anaesthesia procedure narcotic or sedative agents are administered to render a patient unconscious and to sedate a patient, possibly in combination with analgesics to suppress pain.

One drug from the group of narcotics for example is Propofol (2,6-Diisopropylphenol) which is a short-acting, intravenously administered hypnotic agent used to induce and maintain general anaesthesia, sedation for mechanically ventilated adults and procedural sedation. Other drugs may be analgesics, such as opioids, for example Remifentanil, Fentanyl or Morphine.

Within anaesthetic procedures, an anaesthesiologist, besides choosing an appropriate drug for the purpose of anaesthesia, must choose a suitable dosage for drug administration. In this regard, an overdose of an anaesthetic drug may have severe consequences for the health of a patient, whereas too low a dose may lead to an incomplete anaesthesia such that a patient potentially may maintain his conscience. One approach to administer an anaesthetic drug to a patient is the so-called target controlled infusion (TCI). Within conventional TCI algorithms a target concentration in the bloodstream (corresponding to the plasma compartment) of the patient is set, and taking into account the age, weight, height and gender of the patient it is calculated what dosage needs to be administered to the patient in order to reach the target concentration in the blood in a reasonably short period of time.

Such algorithms have been developed based on small patient groups. They are not specific to the patient's individual physiology, and therefore the pharmacokinetics (indicating the distribution of a drug within a patient over time) and the pharmacodynamics (indicating the effect of the drug over time) based on a so called PK/PD model is not very precise. TCI algorithms in general have an accuracy of about ±25%, wherein deviations from the specified target concentration may even be higher for patients with high fat mass, for patients with organic dysfunctions or for children.

Well-established EEG monitoring devices (bi-spectral monitor devices BIS) are measuring the actual effect of an anaesthetic drug agent through an index value that corresponds to the depth of anaesthesia without giving any predictive information. In general such monitoring data do not allow calculating a drug concentration in the patient's compartments because they are not specific to individual drugs. In general, the index value is a signal that is affected by the influence of multiple drugs. The index value does not allow calculating the pharmacokinetics or pharmacodynamics of individual drugs in dependence of changing drug dose rates due to cross correlation effects.

Currently, no monitoring devices for frequently measuring the actual drug concentration in compartments of a patient are commercially available which would allow to calculate the kinetics of this drug and which would support the anaesthetist's decisions with predictive information about the depth of an anaesthesia.

There is a need for a technique to allow for a control of drug administration to a patient over time which in a more exact fashion takes into account information about a drug concentration reached in a compartment of interest, for example the brain compartment, when administering an anaesthetic drug within an anaesthesia procedure.

EP 1 610 681 B1 discloses an anaesthetic agent delivery system for intravenously delivering a desired dose of an anaesthetic agent to a patient. The system comprises an intravenous anaesthetic supply, a breath analyzer analyzing a patient's breath for a drug concentration contained therein and outputting a signal indicating the drug concentration, and a control device receiving the signal and controlling the supply based on the signal.

Within a method known from DE 10 2006 045 014 A1 a concentration of a drug within the breath of a patient is measured and compared with a calculated, predicted concentration in the breath. If the dosage of the drug administered to the patient is changed, the concentration range in which the concentration measured in the breath must lie is adapted.

DE 103 35 236 B3 a measurement system for determining the concentration of Propofol in the breath is known. The system comprises a breathing line having a breathing sensor connected to an analyzing unit. The analyzing unit, in dependence on a signal of the breathing sensor, activates a pump of a Propofol sensor to take a breathing probe such that the Propofol sensor outputs a measuring signal indicative of the concentration of the Propofol to the analyzing unit.

Within a method known from WO 2005/072792 A1 data from a patient during delivery of medication is sampled, and in a closed-loop process a medication response profile from the sampled data is repeatedly updated by updating parameters of the medication response profile. Such parameters are indicative of changes in a patient's response to the delivery of the medication.

It is an object of the invention to provide a method and a control device which allow for an improved control of the kinetics and dynamics of a drug administration procedure, in particular when administering an anaesthetic drug such as Propofol within an anaesthesia procedure.

This object is achieved by a method comprising the features of claim 1.

Accordingly, a method of operating a control device for controlling an infusion device for administering a drug to a patient comprises the steps of:
(a) providing a model to predict a time-dependent drug concentration in multiple compartments of a patient;
(b) setting a target concentration value to be achieved in at least one of the compartments of the patient;
(c) determining a drug dosage to be administered to a first compartment of the multiple compartments of the patient using the model such that the difference between the target concentration value and a predicted steady-state drug concentration in the at least one of the compartments is smaller than a pre-defined threshold value;

(d) providing a control signal indicative of the drug dosage to an infusion device for administering the drug dosage to the patient;

(e) obtaining at least one measurement value indicating a measured drug concentration in at least a second compartment of the multiple compartments at one or more measurement times;

(f) adjusting the model such that the model predicts a drug concentration in at least the second compartment at the one or more measurement times which at least approximately matches the measured drug concentration in at least the second compartment; and (g) determining a new drug dosage to be administered into the first compartment of the patient using the model such that the difference between the target concentration value and a predicted steady-state drug concentration in the at least one of the compartments is smaller than the pre-defined threshold value.

Not all steps necessarily must be carried out in the specified sequence. Some steps may for example also be carried in a different order or at the same time as other steps, such that the sequence as stated in the claims shall not be limiting for the scope of the invention.

It however may be beneficial to carry out the steps in the specified order.

The term "threshold" in this regard is to be understood as defining a bandwidth of tolerance around the desired target concentration. The drug dosage hence is determined such that the predicted steady-state drug concentration falls into that acceptable bandwidth. For this, in particular the absolute value of the difference is observed and shall be smaller than the acceptable threshold.

The instant invention is based on the idea to use a model, such as a pharmacokinetic-pharmacodynamic (PK/PD) model, to predict a drug concentration as a function of time in multiple compartments of a patient. Such prediction model is used to associate a measured drug concentration value indicative of a drug concentration in a second compartment, for example a lung compartment or brain compartment of a patient, with a drug concentration in a first compartment, for example a plasma compartment of the patient. Hence, from measuring the drug concentration in the second compartment it can be concluded what (approximately) the drug concentration in the compartments of the patient is such that the drug concentration in at least one of the compartments may be controlled to bring it close to a desired target concentration value.

Beside the visualization of actual monitoring information about a drug concentration in a compartment, this technique is capable to recalibrate the (PK/PD) model with patient individual monitoring information. The recalibrated model allows a predictive view of compartment concentration in dependence of an actual drug dose rate profile administered to a patient. The predictive view may deliver information about the quality of asymptotic alignment between recalculated compartment concentrations and pre-determined target concentrations over time. Upon obtaining an (inacceptable) deviation between a calculated final steady state compartment concentration and the pre-determined target concentration, by means of the technique a corrective dose rate profile to sufficiently improve the asymptotic fit conditions within a minimal period of time can be calculated. In case that an anaesthetist changes a target concentration, the technique is able to calculate a new drug dosage to fulfil the new fit requirements between the recalculated drug concentrations versus the new target concentration in the compartments. The technique hence presents an efficient supporting tool for the anaesthetist with a predictive view on the kinetics and dynamics of the drug.

The method starts from an initial model which is used to determine a first drug dosage to be administered to the patient. Such initial model is based on empirical data and takes into account demographic information such as the age, weight, height, gender or other data relating to the patient to which the drug shall be administered. Upon administering the first drug dosage determined by means of the initial model, it is measured what drug concentration results in the second compartment, for example in the lung compartment. For this, the drug concentration can for example be measured in the breath of the patient such that a reliable value for the drug concentration in the second compartment, for example the lung compartment, is obtained. Alternatively, or in addition an EEG index value can be measured such that a reliable value for the drug concentration in the second compartment, for example the brain, is obtained. The EEG index value is valid to obtain a reliable value for the drug concentration in the brain compartment if no other drugs are administrated in parallel that affect the EEG index value.

Upon obtaining such measurement value, the model predicting the time-dependent drug concentrations in the different compartments of the patient is adjusted such that it fits the measurement value actually measured in the second compartment. Time retardations in between the compartment concentrations herein are inherently covered by the model. Based on the adjusted model then a new drug dosage for administration into the first compartment, e.g the plasma compartment, of the patient is calculated such that by administering the new drug dosage to the patient the drug concentration in one of the compartments, for example the brain compartment of the patient, is brought close to the target concentration value (i.e. it in a steady-state condition lies in an acceptable range around the target concentration value).

The term "drug dosage" herein generally is to be understood as a drug dosage profile, i.e. a time-dependent profile of the dose rate to be administered to the patient (rate-over-time profile). A drug dosage profile may have the shape of a rectangle or an arbitrary time-dependent curve.

In this regard, the steady-state drug concentration corresponds to the drug concentration at a time after a steady-state condition exhibiting only minor variations in the drug concentration level is reached.

Within the model, for example within a pharmacokinetic-pharmacodynamic model, the patient's body is logically divided into multiple compartments between which an exchange of the drug takes place. A patient comprises for example a lung compartment corresponding to the patient's lung, a brain compartment corresponding to the patient's brain, a plasma compartment corresponding to the patient's blood cycle, a muscle compartment corresponding to the patient's muscles and organs, a fat compartment corresponding to the patient's fat and connective tissue, and possibly also other compartments. Within an anaesthesia procedure, an anaesthetic drug such as Propofol, Fentanyl, Remifentanil and/or a muscle relaxant drug is intravenously injected into the plasma compartment of the patient and, hence, upon injection enters the blood stream of the patient. From the blood stream, the drug is distributed within the patient's body and enters other compartments of the patient, for example the lung compartment and the brain compartment. Within the model, the transfer of the drug from one compartment to another can for example be described by so-called transfer rate constants which indicate the transfer rate between the compartments.

Within a pharmacokinetic-pharmacodynamic model, for example, transfer rate constants indicate the transfer rate between the plasma compartment and the lung compartment, the brain compartment and other compartments. Time retardations of concentrations in the different compartments are defined through these transfer rate constants. Herein, the plasma compartment represents a link mechanism between the different compartments in that a drug exchange primarily takes place between the plasma compartment and the lung compartment and between the plasma compartment and the brain compartment, for example, but not directly between the lung compartment and the brain compartment. The volumes of the compartments are also taken into account in the model.

Pharmacokinetic-pharmacodynamic models as such are known in the art and are described for example in WO 2005/084731 A2, whose contents shall be incorporated by reference herein, or by M. Coppens et al. in "Study of the time course of the clinical effect of propofol compared with the time course of the predicted effect-side concentration: performance of three pharmacokinetic-dynamic models", British Journal of Anaesthesia, 104 (4): 452-8 (2010) and by J.-O. Hahn et al. in "A direct dynamic dose-response model of propofol for individualized anaesthesia care", IEEE Transactions on Biomedical Engineering, vol. 59, no. 2, February 2012.

By means of the proposed method a prediction model for predicting a time-dependent drug concentration in different compartments of a patient is—starting from an initial model which is based on empirical data and initial demographic information about patient—personalized by iteratively in at least the adjusting the model in accordance with measured drug concentration values second compartment, for example the lung compartment, of the patient. For the iterative personalization of the model, steps (d) to (g) may iteratively be repeated throughout a control procedure, such that iteratively the drug concentration in the second compartment of the patient, for example the lung compartment, is measured at different measurement times, and based on such measured drug concentration values the model is iteratively adapted. By means of the measured drug concentration values, hence, the model is adjusted to reflect the personal conditions and behavior within the particular patient with regard to the exchange and distribution of a drug between the different compartments of the patient. Hence, by personalizing the model in accordance with measurement values specifically measured for a patient during an administration procedure the model becomes more accurate and allows for a more exact prediction of the actual drug concentration in a compartment of interest, for example in the brain compartment in which an anaesthetic drug such as Propofol causes its effects for the anaesthesia of the patient.

The fit variables for optimizing the model during the method may for example be mainly driven through the volumes for fat and muscle mass while the overall mass shall be constant. The most sensitive compartments are muscle mass (metabolism makes a drug such as Propofol disappear) and fat mass which have an influence on plasma concentration. Propofol for example is lipophilic and therefore preferably stored in fat mass. The muscle and fat volumes hence may be the first choice variables, e.g. for administering Propofol, to recalibrate the PK/PD model. The related transfer coefficients for muscle and fat may be second choice variables to recalibrate the model due to the fact that they are predetermined by physiological measurements. The brain volume and the transfer coefficients between the plasma compartment and the brain compartment are preferably not considered to be used as fit variables. The physiological values for the brain should preferably be kept, hence presenting boundaries which reduce the variability in the system and increase the convergence speed.

The physiological values for the lung might be also used as fit variables, in case that the drug concentration value indicative of a drug concentration in a second compartment, is measured in parallel for example in the lung compartment and the brain compartment of a patient. Other variables might be preferred for drugs or patients with respect to their known specific physiological behavior.

The method preferably is carried out by a control device which is operated according to the steps of the method. The measurement value herein is taken by a measurement device connected to the control device, the measurement device being constituted to measure a drug concentration in the patient's breath or to measure a signal indicative to a drug concentration in the patient's brain.

The measurement value may for example be obtained by continuously measuring the drug concentration in the patient's breath over a predetermined number of breathing cycles and by averaging the measured drug concentration throughout the different breathing phases. For the measurement it hence is not distinguished between the separate breathing phases, but the measurement takes place continuously over all breathing phases.

Alternatively, it may also be distinguished between the breathing phases and the concentration of the drug, for example Propofol, in the patient's breath may be measured only during exhalation and hence only in the end-tidal exhaled breath.

The number of predetermined breathing cycles may for example be six. However, also other numbers of breathing cycles over which a measurement is taken are conceivable, for example two breathing cycles, four breathing cycles or eight breathing cycles.

Alternatively, the measurement may done continuously with a high time resolution to measure the time-varying drug concentration (with its ups and downs) during a single breath cycle.

Alternatively, the measurement value may for example be obtained by an EEG index value in the patient's brain.

The control device provides a control signal indicative of a drug dosage profile to an infusion device, which hence is commanded to inject the indicated drug dosage to the patient. The infusion device is for example a computer-controlled infusion pump such as a syringe pump which intravenously injects the drug dosage into the blood stream of the patient and hence into the plasma compartment of the patient.

Herein, the first measurement value beneficially is taken after the administration of the drug dosage to the patient nearly reaches a continuous flow rate status or is completed and a homogeneous distribution of the drug in the blood-stream is reached. For example, the control device may command the infusion device to administer a drug dose profile over a specific time window. When the administration of the drug dosage over this time window nearly reaches a continuous flow rate status or is nearly completed, another measurement is taken, and according to the obtained measurement results the model is adjusted to obtain a better fit with the measurement results.

The drug concentration is measured beneficially in the patient's breath to obtain an indication of the actual drug concentration in the lung compartment. However, what information is actually needed is not the drug concentration in the breath, but a value for the drug concentration in the lung compartment. Hence, a transformation of a measurement signal e.g. indicating the drug concentration in the exhaled air into a drug concentration of the lung compartment must be performed. For this, a transformation function is used which serves to transform the measured signal (obtained from measurement on the patient's breath) into a measurement value indicating the actual drug concentration in the lung compartment. The transformation function acts in the second compartment where the measurement is done to avoid time retardations.

An equivalent transformation may also be used in case that the measurement value is an EEG index value which is to be transferred into a drug concentration value in the brain compartment, provided that the administered drug is the only one that affects the EEG index value.

The transformation function advantageously is generated beforehand (i.e. prior to carrying out the actual method) within a prospective study for this the following steps are carried out in case that a measurement value is generated in the patient's breath:

- Within a prospective study, a drug is administered such that a steady-state condition is nearly achieved, i.e. a multi-compartment PK/PD model indicates an equilibrium in which the drug concentrations in the different compartments no longer change over time (this is done to minimize time retardation effects between the different compartments).
- A measurement is taken in the patient's breath (measuring for example Propofol in the patient's breath) generating a measurement information at a time when steady-state conditions have been reached.
- At the same time a blood sample is taken, and the drug concentration is measured in the blood sample through lab equipment, hence obtaining an exact value for the drug concentration in the plasma compartment.
- The PK/PD model is calibrated in a way that the calculated drug concentration in the plasma compartment becomes identical to the measured drug concentration in the blood sample.
- The calibrated PK/PD model is used to calculate the drug concentration in the lung compartment at the measurement time, hence obtaining a measurement signal at the measurement time corresponding to the actual drug concentration in the lung compartment at the measurement time. By setting the actual drug concentration and the measured signal in relation, a transfer function without time retardation is obtained which may serve to transform the measured signal indicating a drug concentration for example in the patient's breath into a measurement value indicating the actual drug concentration in the lung compartment.
- The steps may be repeated for different steady-state conditions (different continuous dose rates) to complete the transfer function for a range of different steady-state conditions.

The transfer function is generated under nearly steady-state conditions with a prospective study and stored in the system. During an actual drug administration procedure, the transfer function is then used with a patient to convert the signals measured for example in the patient's breath into a drug concentration value in the lung compartment in knowledge of the drug dose rate profile and by using the PK/PD model under general conditions.

Equivalent steps might be carried out in case that the measurement value is an EEG index value in the brain compartment and the administered drug is the only one that affects the EEG index value.

The transfer function hence is predefined through a prospective study. The transfer function might be stored in the measurement device or in the control device (also denoted as infusion manager). It transforms for example a Propofol concentration in exhaled air into a lung concentration of Propofol, thus representing a link between the measurement and the PK/PD model. Herein, the transfer function links the measurement signal (e.g. obtained in exhaled air) with the related concentration in the associated compartment in which the measurement has been carried out. This avoids time retardations effects and allows to use a simple transfer function between a measured signal and an associated drug concentration in the associated compartment (e.g. the lung compartment) at any time.

The object is furthermore achieved by a control device for controlling an infusion device for administering a drug to a patient, the control device being constituted to:

(a) provide a model to predict a time-dependent drug concentration in multiple compartments of a patient;
(b) set a target concentration value to be achieved in at least one of the compartments of the patient;
(c) determine a drug dosage to be administered to a first compartment of the multiple compartments of the patient using the model such that the difference between the target concentration value and a predicted steady-state drug concentration in the at least one of the compartments is smaller than a pre-defined threshold value;
(d) provide, as an output, a control signal indicative of the drug dosage to an infusion device for administering the drug dosage to the patient;
(e) obtain, as an input, at least one measurement value indicating a measured drug concentration in at least a second compartment of the multiple compartments at a measurement time;
(f) adjust the model such that the model predicts a drug concentration in at least the second compartment at one or more measurement times which at least approximately matches the measured drug concentration in at least the second compartment; and
(g) determine a new drug dosage to be administered into the first compartment of the patient using the model such that the difference between the target concentration value and a predicted steady-state drug concentration in the at least one of the compartments is smaller than the pre-defined threshold value.

The advantages and advantageous embodiments described above for the method in an analogous fashion also apply to the control device such that it shall be referred to the above description.

In an advantageous embodiment the control device preferably is constituted to request, as an input prior to step (d), a user confirmation before providing the control signal to the infusion device. Hence, the control device is constituted to execute the method as a so called open-loop system in which an optimization of the model and the output of control signals to control an infusion device takes place under user control by means of user interactions. In particular, the control device may propose to administer a new drug dosage to a patient, wherein the new administration must be confirmed by a user, in particular an anaesthesiologist, such that no automatic drug administration takes place.

In principle, however, it is also conceivable to operate the control device and its attached peripheral devices as a closed-loop system in which automatically measurements are taken, the model is optimized and adjusted drug dosages are administered to a patient.

The control device may be a separate device in addition to the infusion device and a suitable monitoring device. It shall be understood however that the control device might not be a separate device, but might be integrated into the infusion device or the monitoring device or all devices may be integrated into one single device.

The method and the control device described above beneficially are suited to control the administration of an anaesthetic drug such as Propofol and/or an analgesic drug such as Fentanyl, Remifentanil or a muscle relaxant drug to a patient in the course of an anaesthesia procedure. In principle, however, the method and the control device may also be used to administer other drugs such as antibiotics or oncology drugs to a patient. With the proposed approach, in addition, also procedures in which multiple drugs such as Propofol and Remifentanil are administered at the same time can be controlled including the monitoring of their cross correlation. Also, a dialysis status, a bacteria concentration or a sepsis may be monitored by the proposed approach.

The idea underlying the invention shall subsequently be described in more detail with regard to the embodiments shown in the figures. Herein:

FIG. 1 shows a schematic drawing of a setup as it generally is used for example in an anaesthesia procedure for administering an anaesthetic drug such as Propofol to a patient P. In this setup multiple devices are arranged on a rack 1 and are connected via different lines to the patient P.

Figure 1:
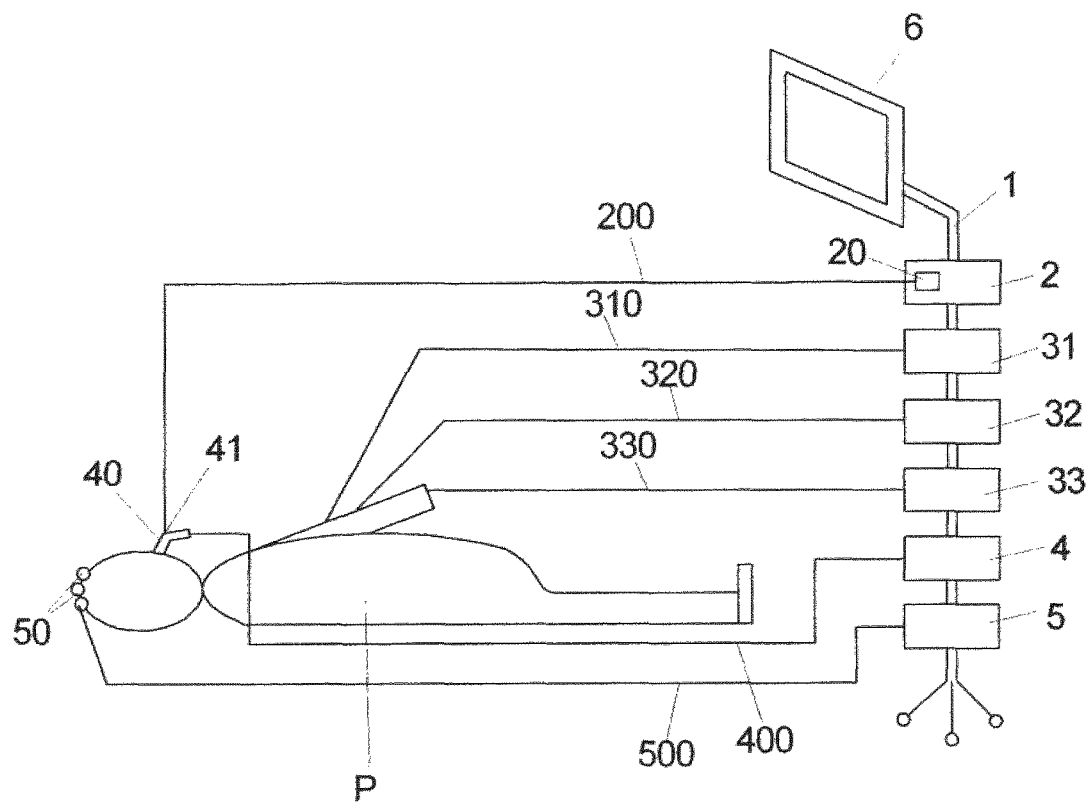
FIG. 1 shows a schematic view of a setup in an anaesthesia procedure.

In particular, infusion devices 31, 32, 33 such as infusion pumps, in particular syringe pumps or volumetric pumps, are connected to the patient P and serve to intravenously inject, via lines 310, 320, 330, different drugs such as Propofol, Fentanyl and/or a muscle relaxant drug to the patient P in order to achieve a desired anaesthetic effect. The lines 310, 320, 330 are for example connected to a single port providing access to the venous system of the patient P such that via the lines 310, 320, 330 the respective drugs can be injected into the patient's venous system.

The rack 1 furthermore holds a ventilation device 4 for providing an artificial respiration to the patient P while the patient P is under anaesthesia. The ventilation device 4 is connected via a line 400 to a mouth piece 40 such that it is in connection with the respiratory system of the patient P.

The rack 1 also holds an EEG monitor 5 which is connected via a line or a bundle of lines 500 to electrodes 50 attached to the patient's head for monitoring the patient's brain activity during an anaesthesia procedure.

In addition, a control device 2 is held by the rack 1 which comprises a measurement device 20 connected to a junction 41 of the mouth piece 40 via a line 200. The control device 2 serves to control the infusion operation of one or multiple of the infusion devices 31, 32, 33 during the anaesthesia procedure such that infusion devices 31, 32, 33 inject anaesthetic drugs to the patient P in a controlled fashion to obtain a desired anaesthetic effect. This shall be explained in more detail below.

The measurement device 20 serves to measure the concentration of one or multiple anaesthetic drugs in the breath of the patient P. The measurement device 20 may for example measure the Propofol concentration in the patient's P exhaled breath. The measurement device 20, for this, may for example continuously measure over a pre-defined number of breathing cycles (inhalation and exhalation), for example six breathing cycles, in order to then suitably average the measured concentration in the patient's P breath over the breathing cycles. Alternatively, the measurement device 20 may also measure the concentration of for example Propofol only during exhalation phases, wherein a suitable triggering mechanism for triggering the measurement may be used, or it continuously measures the Propofol concentration.

Optionally, the EEG monitor 5 measures alternatively or in parallel an index value that quantifies the effect (depth of anaesthesia) in the brain.

The control device 2 may be adapted to provide information about a measured drug concentration in the patient's P breath or in other compartments of the patient P, or information about the drug effect in patient's brain compartment. Such information can be output via a monitor 6 attached to the rack 1 such that personnel, such as an anaesthesiologist, may monitor a drug concentration and the related effect achieved in the patient P during an anaesthesia procedure.

Figure 2:
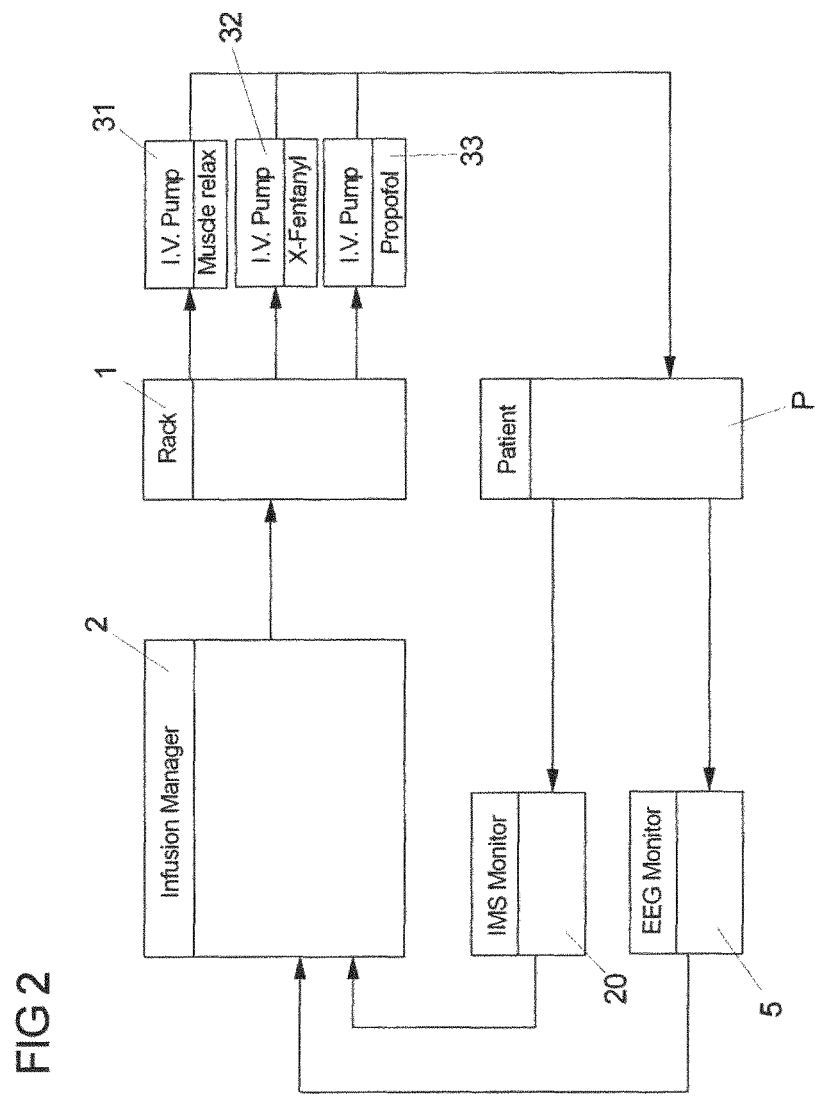
FIG. 2 shows a functional diagram of the setup of FIG. 1.

FIG. 2 shows a functional diagram of a control loop for controlling the infusion operation of the infusion devices 31, 32, 33 during an anaesthesia procedure. The control loop herein may in principle be set up as a closed loop in which the operation of the infusion devices 31, 32, 33 is automatically controlled without user interaction. Beneficially, however, the system is set up as an open-loop system in which at certain points of time, in particular prior to administering a drug dosage to a patient, a user interaction is required in order to manually confirm the operation.

The control device 2, also denoted as "infusion manager", is connected to the rack 1 which serves as a communication link to the infusion devices 31, 32, 33 also attached to the rack 1. The control device 2 outputs control signals to control the operation of the infusion devices 31, 32, 33, which according to the received control signals inject defined dosages of drugs to the patient P.

By means of the EEG monitor 5 an EEG reading of the patient P is taken, and by means of the measurement device 20 the concentration of one or multiple drugs in the patient's P breath is measured. The measured data obtained by the EEG monitor 5 and the measurement device 20 are fed back to the control device 2, which correspondingly adjusts its control operation and outputs modified control signals to the infusion devices 31, 32, 33 to achieve a desired anaesthetic effect.

The measurement device 20 may for example be constituted by a so called IMS monitor for measuring a drug concentration in the patient's P breath by means of the so called Ion Mobility Spectrometry. Other sensor technologies may also be used.

The control device 2 uses, to control the infusion operation of one or multiple infusion devices 31, 32, 33, a pharmacokinetic-pharmacodynamic (PK/PD) model, which is a pharmacological model for modelling processes acting on a drug in the patient's P body. Such processes include the resorption, the distribution, the biochemical metabolism and the excretion of the drug in the patient's P body (denoted as pharmacokinetics) as well as the effects of a drug in an organism (denoted as pharmacodynamics). Preferably, a physiological PK/PD model with N compartments is used for which the transfer rate coefficients have been experimentally measured beforehand (for example in a proband study) and are hence known. To simplify the model not more than 4-5 compartments preferably are used.

Figure 3:
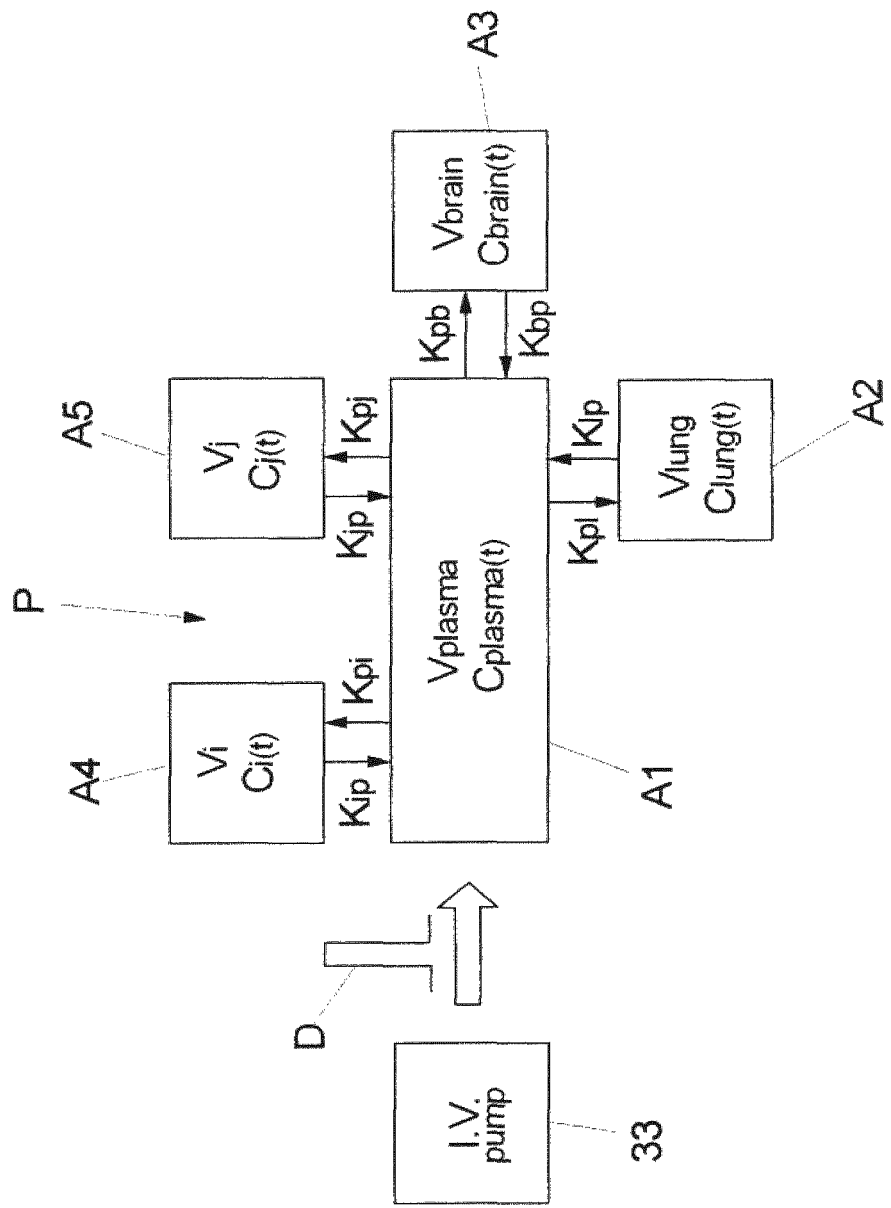
FIG. 3 shows a functional diagram of a model for modelling the distribution of a drug dosage in a patient's body.

A schematic functional drawing of the setup of such a model p is shown in FIG. 3. The model p logically divides the patient P into different compartments A1-A5, for example a plasma compartment A1 corresponding to the patient's P blood stream, a lung compartment A2 corresponding to the patient's P lung, a brain compartment A3 corresponding to the patient's P brain and other compartments A4, A5 corresponding, for example, to muscular tissue or fat and connective tissue. The model p takes into account the volume $V_{Lung}$, $V_{plasma}$, $V_{brain}$, $V_i$, $V_j$ of the different compartments A1-A5 as well as transfer rate constants $K_{PL}$, $K_{LP}$, $K_{BP}$, $K_{PB}$, $K_{IP}$; $K_{PI}$, $K_{JP}$, $K_{PJ}$ indicating the transfer rates between the plasma compartment A1 and the other compartments A2-A5, assuming that a drug dosage D by means on an infusion device 33 is injected into the plasma compartment A1 and the plasma compartment A1 links the other compartments A2-A5 such that an exchange between the other compartments A2-AS always takes place via the plasma compartment A1. The model p serves to predict the concentration $C_{lung}$, $C_{plasma}$, $C_{brain}$, $C_i$, $C_j$ of the injected drug in the different compartments A1-A5 as a function of time.

FIG. 4 to 12 show an embodiment of a procedure for controlling the infusion operation of an infusion device 33 by means of a control device 2. FIG. 4 to 12 herein show different steps of the control procedure, wherein—after an initial phase—the steps may iteratively be repeated such that over a time a desired behavior, advantageously a steady-state condition for the drug concentration e.g. in the brain compartment or plasma compartment of particular interest, is achieved.

The procedure is setup as an optimization (personalization) procedure for the PkPd model due to patient individual conditions in which, at certain measurement times t1, t2, a drug concentration, namely in the lung compartment A2, is measured from the patient's exhaled breath. Alternatively, or additionally, also the EEG index value may be measured in the brain compartment (A2) at times t1, t2 to obtain a measurement value M1, M2 indicating the drug concentration in the patient's brain. Such measurement values M1, M2 are then used to optimize the model p in such a fashion such that it reflects the particular processes and effects within the particular patient P, wherein a drug dosage profile to be administered to the patient P is adjusted in such a fashion that a certain desired drug concentration is reached in a second compartment, namely in the brain compartment A3, alternatively in the plasma compartment A1.

Figure 4:
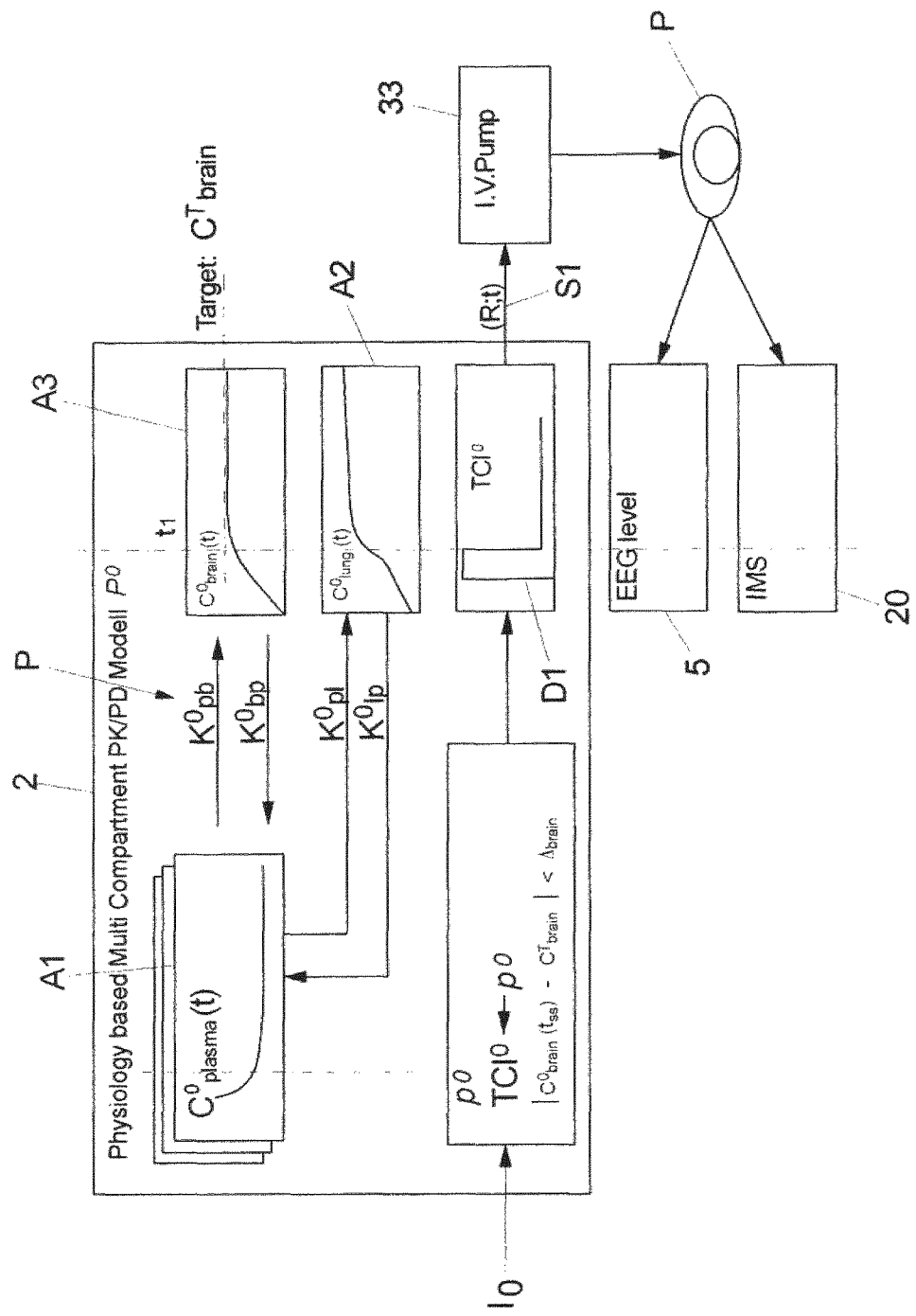
FIGS. 4-12 show different steps of a control procedure for controlling the administration of a drug to a patient.

In a first step, shown in FIG. 4, the model p is initialized by using empirical data and by taking into account demographic information about the patient P such as the patient's P weight, size, gender or body mass index (BMI). Using the first, initial model p0 with its initialized transfer rate constants $K_{OPB}$, $K_{OBP}$, $K_{OPi}$, $K_{OiP}$, indicating the transfer rates between the plasma compartment A1 and the brain compartment A3 and the plasma compartment A1 and other compartments A2, A4, A5, then, a first drug dosage profile D1 to be administered to the patient P is determined by assuming that a target concentration in the brain, $C^T_{brain}$, shall be reached in the brain compartment A3 in a steady-state condition after having injected the drug dosage Dl. The target concentration $C^T_{brain}$ can manually be set in accordance with an effect to be achieved in the brain by administering the drug. For example, in an anaesthesia procedure, in which Propofol is injected into a patient P a certain Propofol concentration in the brain may be required to achieve a desired anaesthetic effect, such that the target concentration $C^T_{brain}$ is set accordingly.

Alternatively, the target concentrations could be defined in the plasma or lung compartment (not shown in FIG. 4).

As depicted in FIG. 4, the model predicts the drug concentration in the plasma compartment A1, the lung compartment A2, in the compartments A4, A5 and in the brain compartment A3 as a function of time. Upon injection of a drug dosage profile the drug concentration in the plasma compartment A1 decays from an initial, comparatively high value, whereas the concentration in the compartments Ai and in the brain compartment A3 grows until a steady state with negligible change in drug concentration is reached. The first, initial drug dosage profile D1 is chosen such that in the steady-state condition the drug concentration in the brain compartment A3 lies within a distance indicated by threshold value $L1_{brain}$ around the desired target concentration $C^T_{brain}$.

To cause the infusion device 33 to inject the drug dosage profile D1 to the patient P, a control signal S1 is fed to the infusion device 33 where S1 might represent a step function with variable dose rate R(t) and step length L1 t. Accordingly, the infusion device 33 injects the drug dosage profile D1 to the patient P.

Figure 5:
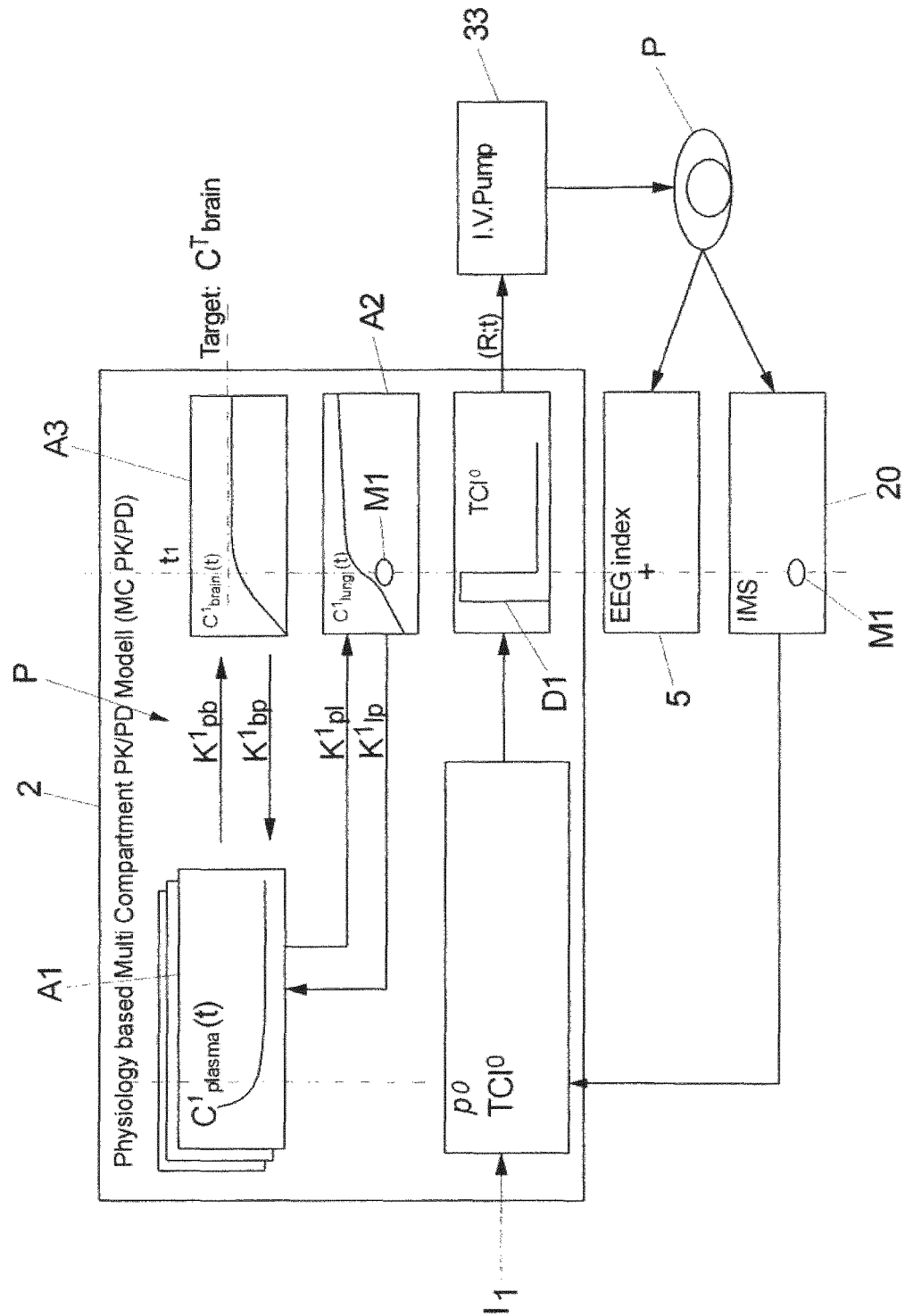

A short time after the drug administration according the dosage profile D1 to the patient P has been initiated (even if steady-state conditions have not yet been reached) a drug concentration is measured in the patient's breath by means of the measurement device 20 and optional the EEG index value is measured by device 5 (FIG. 5). The obtained measurement signal is transformed through a transformation function TF(M1-7 Lung concentration $C^{M1}_{Lung}(t1)$) into a lung concentration at time t1 (measurement value M1), and the actual concentration in the lung compartment $C^{M1}_{Lung}(t1)$ is fed to the control device 2. Alternatively, the measured signal may be fed to the control device 2 and the transfer function may be used within the control device 2 to transform the measured signal in the control device 2 to the measurement value M1 indicating the actual concentration in the lung compartment.

In the next step (FIG. 6) the model p is adjusted by using e.g. a least-squares fit such that the concentration predicted by the model p in the lung compartment A2 at least approximately matches the actually measured drug concentration $C^{M1}_{Lung}(t1)$ (measurement value M1). For this, e.g. in a least-squares fit routine parameters of the model p, in particular the transfer rate constants $K_{PB}$, $K_{BP}$, $K_{Pi}$, $K_{iP}$ and/or the values of the volumes Vi, Vj (see FIG. 3) are adjusted such that the model p predicts a drug concentration curve in the lung compartment A2 at least approximately matching the measurement value M1. Hence, an adjusted model p'1 is achieved, which more accurately models the processes and effects within the particular patient P that already have taken place (retrospective view).

In a next step (FIG. 7), using the adjusted model with its adjusted parameters a new drug dosage profile is determined, wherein the new drug dosage profile is determined in such a manner that—by using the adjusted model—the drug concentration Cbrain in the brain compartment A3 at steady state reaches the desired target concentration $C^T_{brain}$ in a prospective view. (Alternatively, a target concentration $C^T$plasma, Clung may be set also for the plasma compartment A1 or the lung compartment A2 (not shown in FIG. 7).

In the next step (FIG. 8), the new drug dosage profile D2 (denoted as TCI1) is communicated to the infusion device 33 by means of a control signal S2, where D2 might be a step function with variable dose rate R(t) and step length L1 t, whereupon the infusion device 33 injects the drug dosage profile D2 to the patient P.

Figure 9:
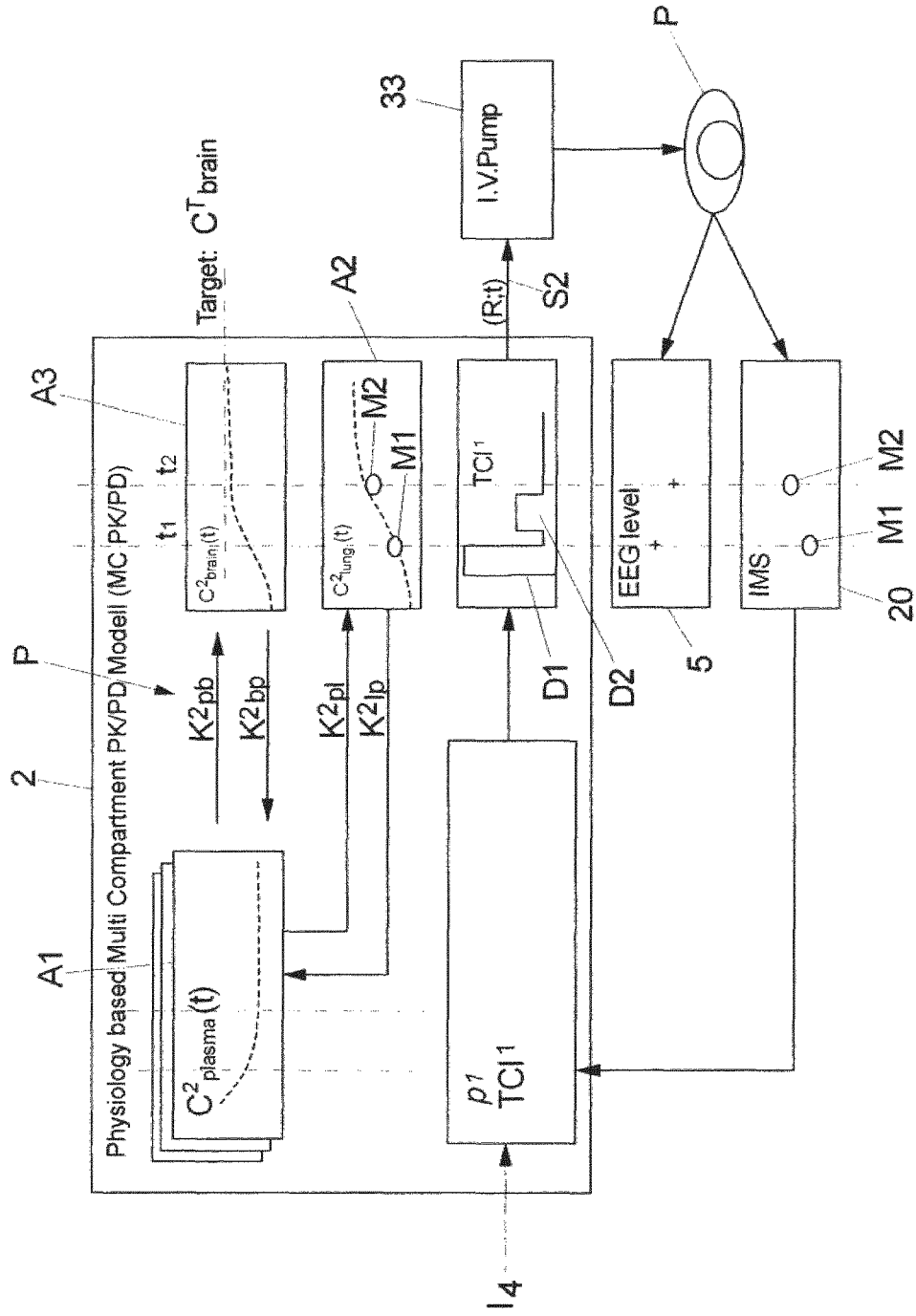
Figure 10:
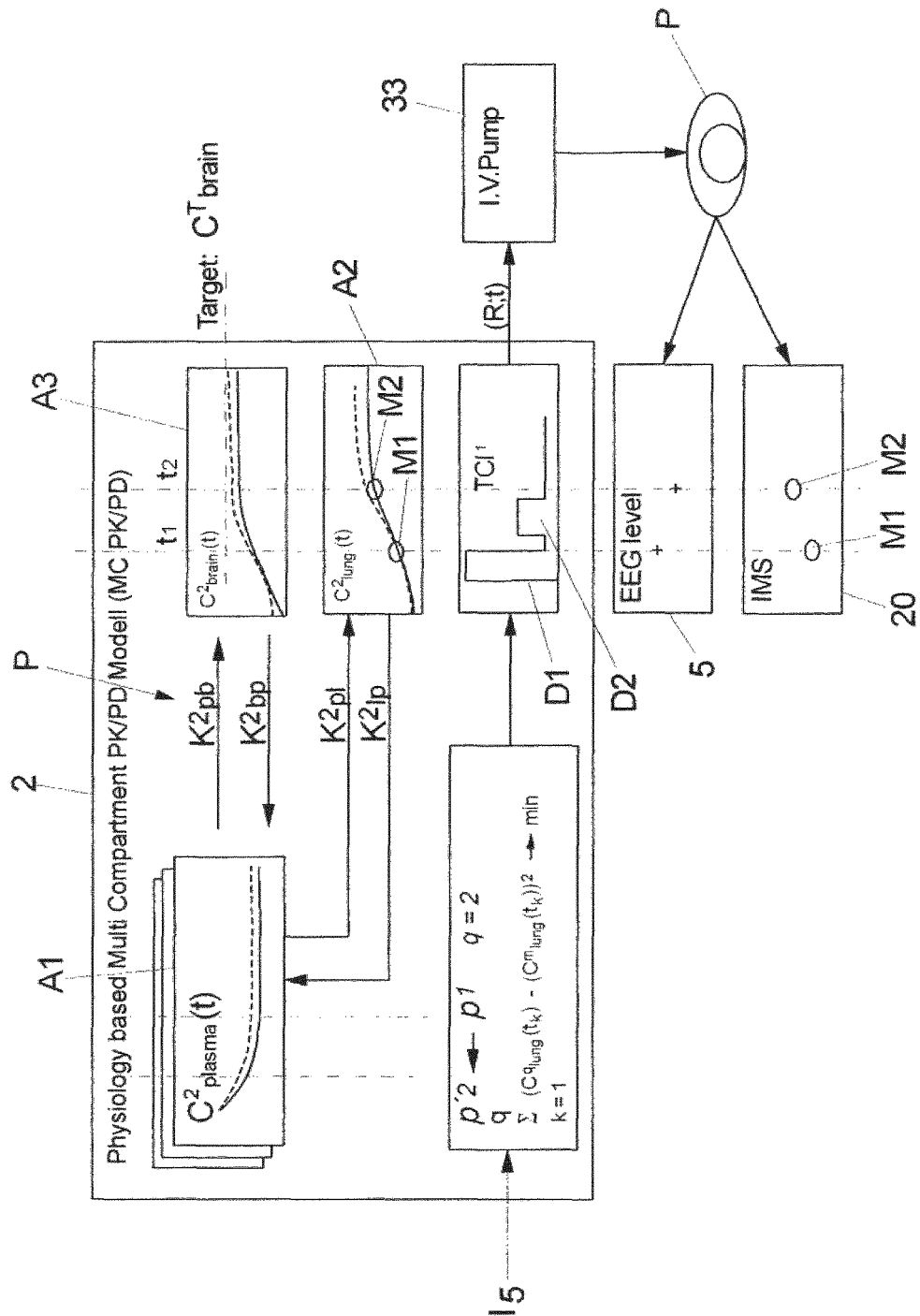

Then, a next measurement value M2 is taken at a second measurement time t2 (FIG. 9). The measurement value M2 again indicates the drug concentration in exhaled air actually obtained in the lung compartment A2, whereupon the model p again is adjusted using a least-squares fit such that the drug concentration curve predicted by the model p for the lung compartment A2 at least approximately predicts all actually measured measurement values M1, M2 (FIG. 10). Due to the adjustment of the model p and its parameters also the predicted drug concentration curves in the other compartments A1, A3-A5 (including the brain compartment A3) change, as depicted in FIG. 10.

In the next step (FIG. 11), the newly adjusted model p is then used to determine another drug dosage profile in such a manner that the drug concentration in the brain compartment A3 at steady state falls within a range around the desired drug concentration target $C^T_{brain}$ indicated by the threshold $L1_{brain}$. (Respectively, the drug concentration in plasma compartment A1 at steady state reaches the target concentration $C^T_{plasma}$.) The newly determined drug dosage profile D3, where D3 might be a step function with variable dose rate R(t) and step length L1 t, is then communicated by means of control signal S3 to the infusion device 33 (FIG. 12) and injected by the infusion device 33 to the patient P.

The steps of FIGS. 9 to 12 may be iteratively repeated to obtain a steady-state drug concentration in the brain compartment A3 which matches the target concentration $C^T_{brain}$, wherein by iteratively adjusting the drug dosages D1, D2, D3 injected into the patient P by means of the infusion device 33 the drug concentration in the brain compartment A3 (respectively in the plasma compartment A1 or the lung compartment A2) may be maintained at the desired target concentration $C^T_{brain}$ (respectively $C^T_{plasma}$ or $C^T lung$) until anaesthesia shall be terminated.

Equivalent steps might be carried out in case that the measurement value is an EEG index value in the brain compartment and the administered drug is the only one that affects the EEG index value. In this case the EEG index value is measured by device 5 (FIG. 5), and the measured index value at time t1 is transformed through a transformation function TF(M1–7 brain concentration $C^M_{brain}(t1)$) into a measurement value M1 for the drug concentration Cbrain in the brain.

The procedure in principle may be set up as a closed-loop procedure not requiring any user interaction.

Figure 6:
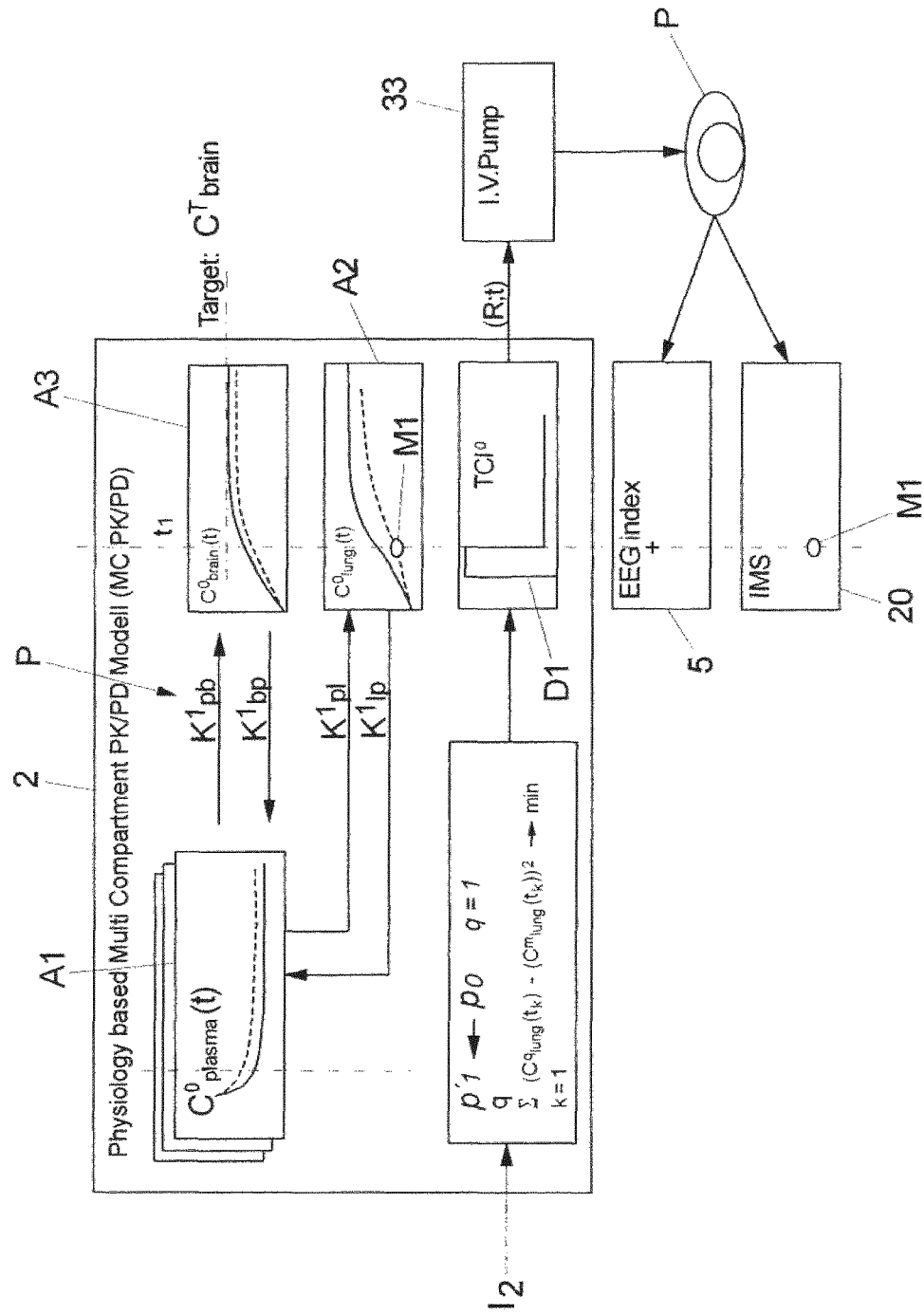
Figure 7:
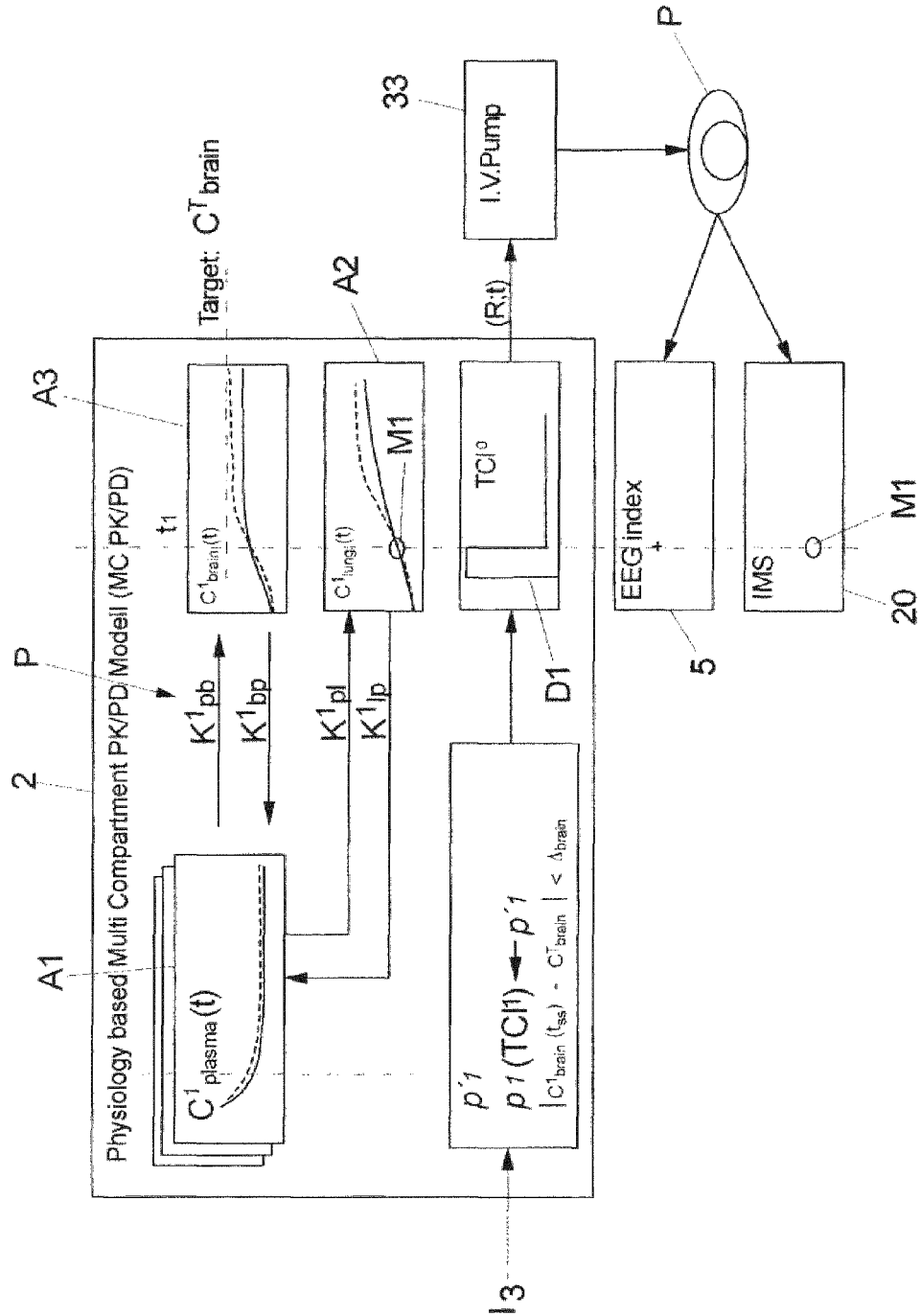
Figure 8:
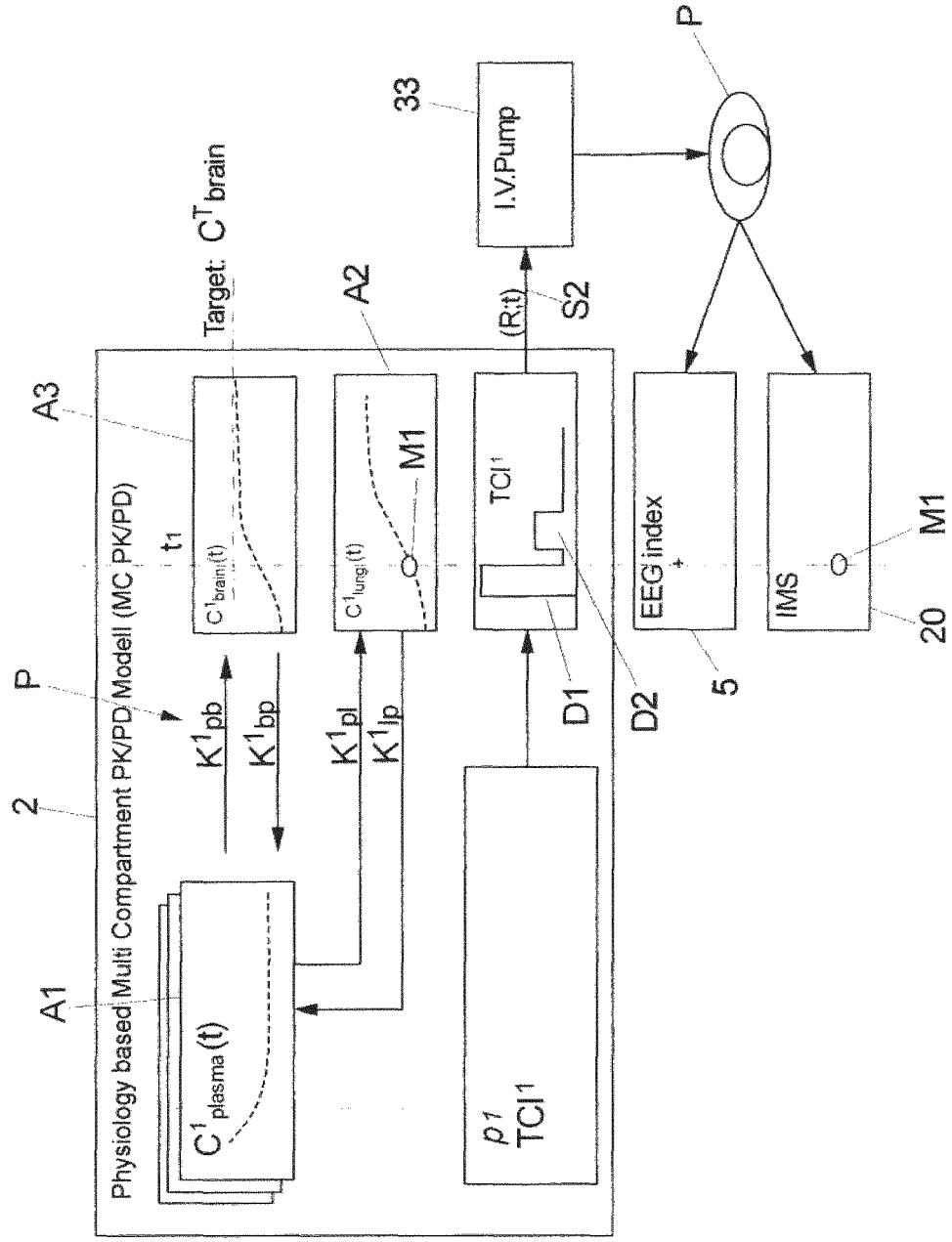
Figure 11:
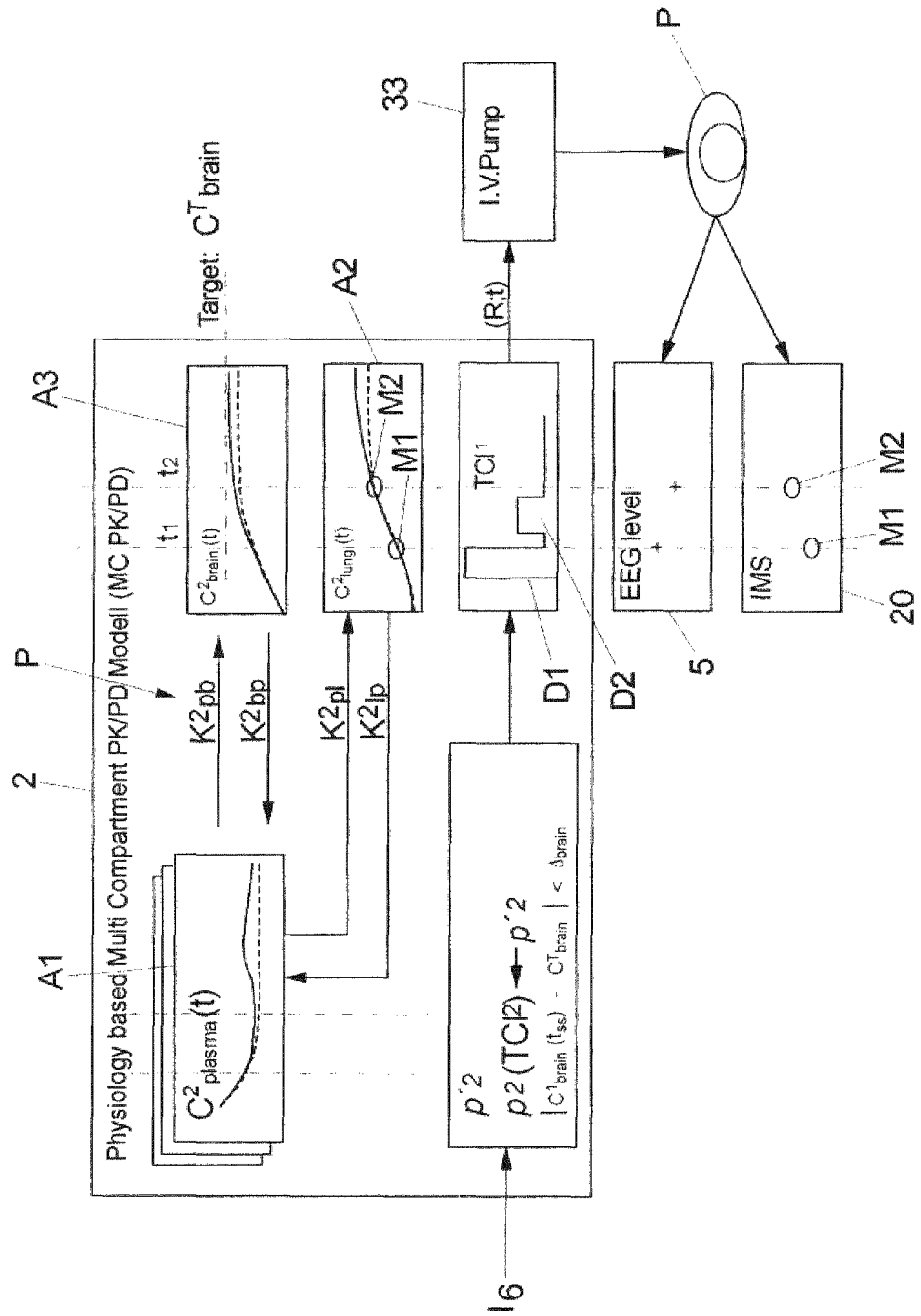
Figure 12:
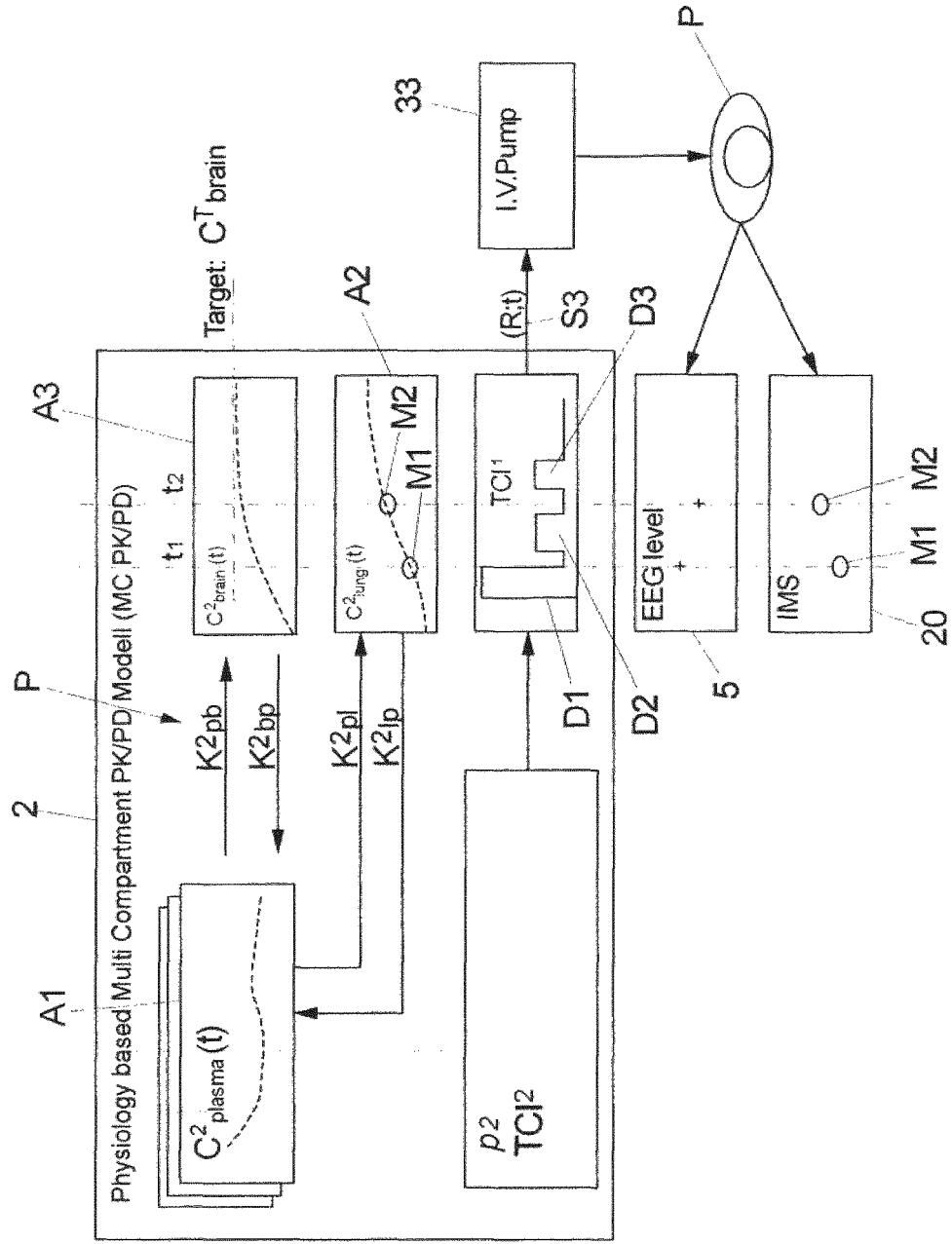

However, beneficially the system is set up as an open-loop system requiring, at certain instances, a user interaction. For example, in the step of FIG. 4 as input I0 demographic information about the patient P such as the patient's P size, gender, weight or body mass index are input by a user. In the step of FIG. 5, as input I1 for example a recalibration request may be input to the control device 2. In the step of FIG. 6, a confirmation for acceptance of the adjusted model p may be input as input I2. In the step of FIG. 7, a confirmation to confirm a newly calculated drug dosage may be required as input I3. In the step of FIG. 9, another recalibration request may be required as input I4. In the step of FIG. 10, a confirmation for acceptance of an adjusted model p may be required as input I5. In the step of FIG. 11, a confirmation of a newly calculated drug dosage may be required as input I6.

It might also happen that the user changes the target concentration during the procedure. In this case the model recalculates a new drug dosage such that the calculated concentration falls within an acceptable range around the newly set target concentration.

It might also happen that the user wants to switch off the pump for the drug administration when the procedure is close to be terminated. In this case the user wants to know when the patient will wake up again, which may be predicted by a prospective view on the drug concentration in e.g. the patient's brain.

It shall be noted that the procedure described herein does not necessarily require a fit with a predetermined target concentration in the brain compartment (which however may be preferred). A target concentration could also be set in other compartments such as the plasma compartment or the lung compartment, and the algorithm for computing a drug dosage to be administered may be carried such that the desired target drug concentration in the plasma or lung compartment is reached. The reason why the brain compartment or the plasma compartment may be preferred to set a target concentration is because a lot of empiric knowledge about necessary target concentrations in the brain compartment and the plasma compartment exist in literature with regard to carrying out an anaesthetic procedure.

It shall further be noted that the measurement values for monitoring an actual drug concentration may be obtained from measuring a drug concentration in the patient's breath or from obtaining an EEG reading. Such procedures (breath monitoring and EEG monitoring) to calibrate the p model are equivalent under the prerequisite that only one drug is administered within a particular procedure. This is due to the fact that the EEG signal is affected by multiple drugs, e.g. Propofol and Fentanyl, if multiple drugs are administered. Therefore, EEG monitoring is not specific in case that various drugs are administered at the same time and the EEG index value cannot anymore be used to calibrate the kinetic models of the individual drugs.

According to a further embodiment of the invention, in a first time interval, measurement values are obtained at one or more measurement times indicating a measured drug concentration in one compartment, preferably the brain compartment A3, and another compartment, preferably the lung compartment A2. Based on the measurement values, the concentration of the drug is calculated in one compartment, preferably the lung compartment A2, by using the respective transformation function and, if the measurement values are obtained for a different compartment, by using a model as described above. In case there is a difference in drug concentration calculated by those two routes, the model and/or, which is preferred, the transformation function could be adapted, so that there is a match between the two results or that the two results are at least within a defined range.

Preferably, based on measurement values obtained at one or more measurement times indicating a measured drug concentration in the brain compartment A3 (for example by using a measurement device for measuring EEG signals) and using a model p, the concentration of the drug in the lung compartment A2 is determined, In addition, the concentration of the drug in the lung compartment is determined based on measurement values obtained at one or more measurement times indicating a measured drug concentration in the lung compartment A2 (for example, by using measurement device for measuring the drug concentration in the patient's breath) by using the respective transformation function TF, which transforms the measured signals indicating a drug concentration in the patient's breath into a measurement value indicating the actual drug concentration in the lung compartment. In case there is a difference between those two values determined for the concentration of the drug in the lung compartment, the transformation function TF which relates the measurement signals obtained by measuring the drug concentration in the patient's breath to the concentration of the drug in the lung compartment is modified, so that the two values in the lung compartment match or are at least within a defined range. This method allows adapting the transformation function TF to the patient. The patient adapted transformation function could be used in the further procedure, improving the overall performance of the method, especially if at a later stage only measurement signals obtained by measuring the drug concentration in the patient's breath are used for adapting the model and/or determining a new drug dosage to be administered.

Of course, this method also applies for other compartments and other transformation functions.

The control device carrying out the model-based optimization algorithm described herein does not necessarily have to be a separate device. It could be part of a monitoring device or it could be part of a pump, or a pump, a monitor device and a control device may be integrated into a single device.

LIST OF REFERENCE NUMERALS

1 Rack
2 Control device
20 Measurement device
200 Line
31, 32, 33 Infusion device
310, 320, 330 Line
4 Ventilation device
40 Mouth piece
400 Line
41 Junction
5 EEG monitor
50 Electrodes
500 Line
6 Display device
A1-A5 Compartments
D, D1-D3 Drug dosage
I0-I6 Input
M1, M2 Measurement value
P Model
P Patient
S1-S3 Control signal

The invention claimed is:

1. A method of operating a control device for controlling an infusion device for administering a drug to a patient, the method comprising the steps of:
   (a) providing a model to predict a time-dependent drug concentration in multiple compartments of a patient;
   (b) setting a target concentration value to be achieved in at least one of the compartments of the patient;
   (c) determining a drug dosage to be administered to a first compartment of the multiple compartments of the patient using the model such that the difference between the target concentration value and a predicted steady-state drug concentration in the at least one of the compartments is smaller than a pre-defined threshold value;
   (d) providing a control signal indicative of the drug dosage to an infusion device for administering the drug dosage to the patient;
   (e) obtaining at least one measurement value indicating a measured drug concentration in at least a second compartment of the multiple compartments at one or more measurement times;
   (f) adjusting the model such that the model predicts a drug concentration in at least the second compartment at one or more measurement times, which at least approximately matches the measured drug concentration in at least said second compartment; and
   (g) determining a new drug dosage to be administered into the first compartment of the patient using the model such that the difference between the target concentration value and a predicted steady-state drug concentration in the at least one of the compartments is smaller than the pre-defined threshold value.

2. The method according to claim 1, wherein the drug is an anaesthetic drug such as Propofol, an analgesic drug such as Fentanil or Remifentanil, or a muscle relaxant.

3. The method according to claim 1 wherein the model is a pharmacokinetic-pharmacodynamic model to predict a drug concentration as a function of time in multiple compartments of a patient.

4. The method according to claim 1, wherein the first compartment is a plasma compartment and the second compartment is a brain or lung compartment.

5. The method according to claim 1, wherein the first compartment is a plasma compartment, the second compartment is a lung compartment and a third compartment is the brain compartment.

6. The method according to claim 1, wherein steps (d) to (g) are iteratively repeated.

7. The method according to claim 1, wherein step (f) includes:
   adjusting at least one transfer rate constant or volume of the model indicating a transfer rate between different compartments or a volume of a compartment.

8. The method according to claim 1, wherein the at least one measurement value is taken by a measurement device which is constituted to measure a drug concentration in the patient's breath.

9. The method according to claim 1, wherein at least one measurement value is obtained by continuously measuring the drug concentration in the patient's breath over a predetermined number of breathing cycles.

10. The method according to claim 1, wherein at least one measurement value is taken by a measurement device which is constituted to measure an EEG signal resulting in an EEG index value.

11. The method according to claim 1, wherein the measurement time of step (e) lies in a range after the administration of the drug dosage by the infusion device indicated by the control signal of step (d) reaches a steady state status in at least the first compartment or is completed.

12. The method according to claim 1, wherein the at least one measurement value at one or more measurement times according to step (e) is obtained before the drug concentration in at least the second compartment reaches a steady state status or is completed.

13. The method according to claim 1, comprising:
   transforming the measurement value into a measured drug concentration in the second compartment at the measurement time using a transformation function.

14. The method according to claim 1, wherein in a further step (h) at least one measurement value is obtained indicating a measured drug concentration in the third compartment of the multiple compartments at one or more measurement times and at least one measurement value is obtained indicating a measured drug concentration in the second compartment of the multiple compartments at one or more measurement times, and a first value indicating a drug concentration in the second compartment is determined based on the measurement values indicating a measured drug concentration in the third compartment by using the model and a second value indicating a drug concentration in the second compartment is determined based on the measurement values indicating a measured drug concentration in the second compartment using a transformation function wherein, in a further step, in case there is a difference between the first value and the second value, the transformation function is adapted, so that the first value and the second value match or are within a defined range.

15. A control device for controlling an infusion device for administering a drug to a patient, the control device being constituted to:
(a) provide a model to predict a time-dependent drug concentration in multiple compartments of a patient;
(b) set a target concentration value to be achieved in at least one of the compartments of the patient;
(c) determine a drug dosage to be administered to a first compartment of the multiple compartments of the patient using the model such that the difference between the target concentration value and a predicted steady-state drug concentration in the at least one of the compartments is smaller than a pre-defined threshold value;
(d) provide, as an output, a control signal indicative of the drug dosage to an infusion device for administering the drug dosage to the patient;
(e) obtain, as an input, at least one measurement value indicating a measured drug concentration in a least a second compartment of the multiple compartments at a measurement time;
(f) adjust the model such that the model predicts a drug concentration in at least the second compartment at the one or more measurement time which at least approximately matches the measured drug concentration in at least the second compartment; and
(g) determine a new drug dosage to be administered into the first compartment of the patient using the model such that the difference between the target concentration value and a predicted steady-state drug concentration in the at least one of the compartments is smaller than the pre-defined threshold value.

16. The control device according to claim 15, wherein the control device is constituted to request, as an input prior to step (d), a user information before providing the control signal to the infusion device.

* * * * *